United States Patent [19]

Carr et al.

[11] Patent Number: 4,820,722

[45] Date of Patent: Apr. 11, 1989

[54] DISUBSTITUTED TETRAZOLES AND THEIR USE AS LEUKOTRIENE ANTAGONISTS

[75] Inventors: F. Patrick Carr, Indianapolis; Robert D. Dillard, Zionsville; Winston S. Marshall, Bargersville; Doris E. McCullough, Carmel, all of Ind.

[73] Assignee: Eli Lilly and Company, Indianapolis, Ind.

[21] Appl. No.: 85,586

[22] Filed: Aug. 14, 1987

[51] Int. Cl.$^4$ .................. C07D 403/06; C07D 257/04; A61K 31/41

[52] U.S. Cl. .................................... 514/381; 548/253

[58] Field of Search ......................... 548/253; 514/381

[56] References Cited

FOREIGN PATENT DOCUMENTS 132366 1/1985 European Pat. Off. .

Primary Examiner—David B. Springer
Attorney, Agent, or Firm—Robert A. Conrad; Leroy Whitaker

[57] ABSTRACT

The instant invention provides disubstituted tetrazoles that antagonizes the effect of leukotrienes $C_4$, $D_4$ and $E_4$ in selected tissues. The disubstituted tetrazoles are used in pharmaceutical formulations and methods of treatment of conditions caused by excessive amounts of leukotrienes $C_4$, $D_4$ or $E_4$ or any combination thereof.

37 Claims, No Drawings

DISUBSTITUTED TETRAZOLES AND THEIR USE AS LEUKOTRIENE ANTAGONISTS

BACKGROUND OF THE INVENTION

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently thought to be major components of what has been previously called slow reacting substance of anaphylaxis (SRS-A).

It is the object of this invention to provide novel chemical agents which are leukotriene antagonists that can be used therapeutically in the treatment of allergic disorders such as asthma, where leukotrienes are thought to be causal mediators. It is a further object of this invention to provide highly potent antagonists whose spectrum of activity is limited to leukotrienes $LTC_4$, $LTD_4$ and $LTE_4$.

SUMMARY OF THE INVENTION

This invention provides for final products of the Formula I

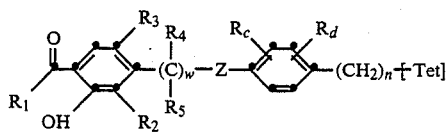

or a pharmaceutically-acceptable base addition salt thereof wherein $R_1$ through $R_5$, n, w, Z, $R_c$, $R_d$ and [Tet] are as defined below.

Another aspect of the invention is intermediate compounds of the Formula II

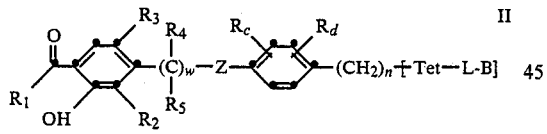

wherein $R_1$ through $R_5$, $R_c$, $R_d$, Z, w, n, and [Tet-L-B] are as defined below, or a pharmaceutically-acceptable base addition salt thereof;

As the instant final products are therapeutic agents, the invention also provides for pharmaceutical compositions (comprised of a therapeutically-effective amount of the compounds of claim 1 and a pharmaceutically-acceptable carrier). Also provided are methods of use for treating asthma specifically, and, in general, diseases caused by the release of an excessive amount of leukotrienes $C_4$, $D_4$, and $E_4$ (both of which comprise administering to said mammal a leukotriene $C_4$, $D_4$, or $E_4$ antagonizing amount the compounds of Formula I.)

DETAILED DESCRIPTION OF THE INVENTION

One aspect of the present invention is the leukotriene $C_4$, $D_4$ and $E_4$ antagonist compounds of the Formula I:

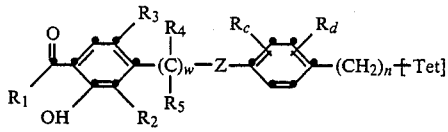

wherein:
$R_1$ is $C_1$ to $C_3$ alkyl;
$R_2$ is $C_1$ to $C_6$ alkyl or $C_3$ to $C_6$ alkenyl;
$R_3$ is a hydrogen atom, chloro, bromo, nitro, or a group of the formula $-NR_aR_b$ wherein $R_a$ and $R_b$ are the same or different and are a hydrogen atom, $C_1$ to $C_4$ alkyl, phenyl, benzyl, or $C_1$ to $C_4$ acyl;
$R_4$ and $R_5$ are the same or different and are a hydrogen atom or $C_1$ to $C_3$ alkyl;
W is from one to six;
Z is O, S or a group of the formula $-NR_e$ (wherein $R_e$ is a hydrogen atom, $C_1$ to $C_4$ alkyl, $C_1$ to $C_4$ acyl, phenyl, or benzyl);
n is 0 to 6;
$R_c$ and $R_d$ are the same or different and are hydrogen, hydroxy, halo or an ether group of the formula $-O-(C_1-C_6 \text{ alkyl})$;
[Tet] is a disubstituted 1H- or 2H-tetrazolyl ring of the formula:

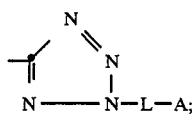

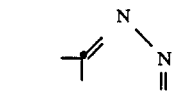

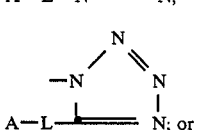

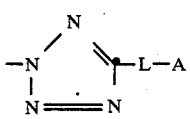

wherein:
L is
(1) $C_1$ to $C_{10}$ alkylidene; or
(2) a group of the formula

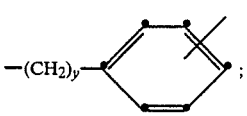

wherein y is 1 to 3 (and the phenyl ring is bonded to A); and

A is
 (1) 5-(tetrazolyl);
 (2) carboxy;
 (3) —NR$_f$R$_g$, wherein R$_f$ and R$_g$ are the same or different and are a hydrogen atom, $C_1$ to $C_4$ alkyl, phenyl, benzyl or $C_1$ to $C_4$ acyl; or
 (4) a group of the formula $$-\overset{\overset{(O)_q}{|}}{(S)}-R_h$$

wherein q is 0, 1 or 2 and R$_h$ is $C_1$ to $C_4$ alkyl, phenyl or benzyl;
or a pharmaceutically-acceptable base addition salt thereof.

In Formula I, the term "$C_1$–$C_6$ alkyl" (or the equivalent term "$C_1$ to $C_6$ alkyl") refers to the straight and branched aliphatic radicals of 1 to 6 carbon atoms such as methyl, ethyl, propyl, isopropyl, butyl, isobutyl, sec-butyl, tert-butyl, amyl, isoamyl, sec-amyl, sec-isoamyl (1,2-dimethylpropyl), tert-amyl (1,1dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like. The term "$C_1$ to $C_6$ alkyl" includes within its definition the definition of the terms "$C_1$ to $C_4$ alkyl" and "$C_1$ to $C_6$ alkyl".

The term "$C_3$–$C_6$ alkenyl" refers to straight and branchd radicals of three to six carbon atoms such as allyl, isopropenyl, butenyl, isobutenyl, 3-methyl-2-butenyl, n-hexenyl, and the like.

The term "$C_1$ to $C_4$ acyl" includes formyl, acetyl, n-propionyl, iso-propionyl, n-butanoyl, sec-butanoyl, iso-butanoyl, and tert-butanoyl. The term "halo" refers to fluoro, chloro, bromo, and iodo.

The term "$C_1$ to $C_{10}$ alkylidene" refers to straight or branched divalent hydrocarbon chains such as —CH$_2$—, —CH(CH$_3$)—, —C(CH$_3$)$_2$—, —CH(C$_2$H$_5$)—, —CH$_2$CH$_2$—, —CH$_2$CH(CH$_3$)—, —CH(CH$_3$)CH$_2$—, —CH(CH$_3$)CH(CH$_3$)—, —CH$_2$C(CH$_3$)$_2$—, —CH$_2$CH(C$_2$H$_5$)—, —CH$_2$CH$_2$CH$_2$—, —CH(CH$_3$)CH$_2$CH$_2$—,—CH$_2$CH(CH$_3$)CH$_2$—, —CH$_2$CH(C$_2$H$_5$)CH$_2$—, —CH$_2$CH$_2$CH(C$_2$H$_5$)—, —C(CH$_3$)$_2$CH$_2$CH$_2$—, —CH(CH$_3$)CH$_2$CH(CH$_3$)—, —CH$_2$CH$_2$CH$_2$CH$_2$—, —CH$_2$C(C$_3$)$_2$CH$_2$CH$_2$—, —CH$_2$C(CH$_3$)$_2$CH$_2$—, —CH$_2$CH$_2$CH(C$_2$H$_5$)CH$_2$—, —CH$_2$CH$_2$CH$_2$CH$_2$—, —CH(CH$_3$)CH$_2$CH$_2$CH$_2$—, —CH$_2$CH$_2$CH$_2$CH$_2$CH$_2$CH$_2$—, —(CH$_2$)$_7$—, —(CH$_2$)$_8$—, —(CH$_2$)$_9$— —(CH$_2$)$_{10}$—, —CH$_2$—CH(CH$_3$)—(CH$_2$)$_4$—, —(CH$_2$)$_2$—CH(C$_2$H$_5$)—(CH$_2$)$_3$—, —CH$_2$—CH(CH$_3$)—(CH$_2$)$_2$—CH(C$_2$H$_5$)—(CH$_2$)$_2$, and the like. The term "$C_1$ to $C_{10}$ alkylidene" includes the definition of straight chain and branched alkylidene groups of the partial formula —CH$_2$)$_n$— (when n is one through 6) that are bonded to the [Tet] group on one end and the phenyl group on the other end in the above Formula I.

The pharmaceutically-acceptable base addition salts of this aspect of the invention include salts derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine, and the like. The potassium and sodium salt forms are particularly preferred with the sodium salt form being the most preferred.

Those skilled in the art will recognize that, when alkyl or alkylidene groups are branched, various stereoisomers will exist. This invention is not limited to any particular stereoisomer but includes all possible individual isomers and racemates of the compounds of Formula I and Formula II. Similarly, when an alkene group is present, both the individual cis and trans isomers and their mixture are included as part of this invention.

A preferred group of the final product compounds of Formula I is composed of compounds wherein:
R$_1$ is methyl;
R$_2$ is n-propyl;
R$_3$, R$_4$, R$_5$, R$_c$, and R$_d$ are a hydrogen atom;
Z is 0;
W is 1;
n is 0 or 1;
[Tet] is a group of the formula:

$$\text{structure with two tetrazole isomers: } \quad \text{—N-L—A; or A—L—N—}$$

L=
 (1) $C_1$ to $C_6$ alkylidene; or
 (2) a group of the formula $$-(CH_2)_y-\langle\text{phenyl}\rangle-$$

wherein y is one (and the phenyl ring is also bonded to A);
A is
 (1) 5-(tetrazolyl);
 (2) a group of the formula —NR$_f$R$_g$ wherein R$_f$ and R$_g$ are each methyl;
 (3) a group of the formula $$-\overset{\overset{(O)_q}{|}}{(S)}-R_h,$$

wherein R$_h$ is methyl; or
 (4) a carboxylic acid;
or a pharmaceutically-acceptable base addition salt thereof.

A more preferred group of the above final product compounds are the bis(tetrazole) compounds wherein the 5-position of the interior tetrazole is bonded to the interior phenyl ring (the ring substituted with R$_c$ and R$_d$) through a methylene group; in other words, wherein A is a 5-(tetrazolyl) ring and n is one. Two preferred groups of the latter bis(tetrazole) compounds are distinguished by the position of the —L—A groups on the interior tetrazolyl ring within the N-2 preferred group is a more preferred group that has L as a methylene, trimethylene, tetramethylene, pentamethylene, hexamethylene, or a 2,2-dimethyl tetramethylene group (bonded through the C-1 position to the A group); or when L is a group of the formula

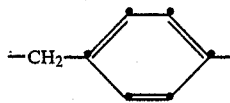

(wherein the phenyl group is also bonded to A).

The most preferred compounds in the immediately preceeding more preferred group occurs when L is C$_3$, in other words, a compound of the Formula III

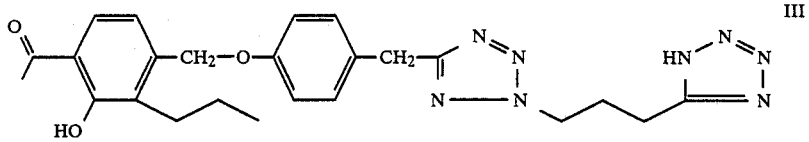

and the corresponding 2-H (exterior tetrazole) isomer, and especially the sodium salt thereof.

A second more preferred group of above (preferred) final product compounds are the exterior carboxy compounds, (i.e., wherein A is carboxy) and the interior tetrazole is bonded at the 5 position to the interior phenyl ring by a methylene group (i.e., n is one). A preferred group of these exterior acid compounds occurs when the exterior linking group L is a straight-chain C$_1$, C$_3$ C$_4$ (methylene, trimethylene or tetramethylene) group. A more preferred group occurs when the straight chain C$_1$, C$_3$ C$_4$ exterior linking group L is bonded at the N-2 position of the interior tetrazole, and especially so when the L group bonded at the N-2 position is trimethylene.

A second aspect of the invention is intermediate compounds of the Formula II.

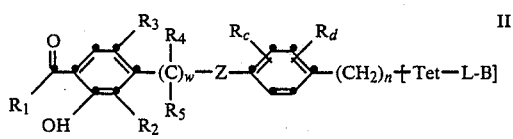

wherein:

R$_1$ is C$_1$ to C$_3$ alkyl;

R$_2$ is C$_1$ to C$_6$ alkyl or C$_3$ to C$_6$ alkenyl;

R$_3$ is a hydrogen atom, chloro, bromo, nitro, or a group of the formula

—NR$_a$R$_b$ wherein R$_a$ and R$_b$ are the same or different and are a hydrogen atom, C$_1$ to C$_4$ alkyl, phenyl, benzyl, or C$_1$ to C$_4$ acyl;

R$_4$ and R$_5$ are the same or different and are a hydrogen atom or C$_1$ to C$_3$ alkyl;

W is from one to six;

Z is O, S or a group of the formula

—NR$_e$, (wherein R$_e$ is a hydrogen atom, C$_1$ to C$_4$ alkyl, phenyl, benzyl or C$_1$ to C$_4$ acyl);

n is 0 to 6;

R$_c$ and R$_d$ are the same or different and are a hydrogen atom, hydroxy, halo or an ether group of the formula —O—(C$_1$—C$_6$ alkyl);

[Tet-L-B] is a disubstituted 1H- or 2H-tetrazolyl ring of the formula

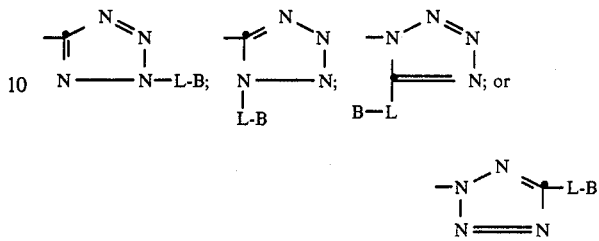

wherein:

L is (1) C$_1$ to C$_{10}$ alkylidene; or (2) a group of the formula

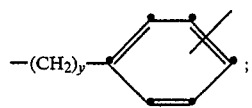

wherein y is 1 to 3 and the phenyl ring is also bonded to B; and

B is (1) cyano;

(2) halo; or (3) a group of the formula —COOR$_6$, wherein R$_6$ is ethyl or a carboxy-protecting group.

In the above Formula II, the terms "C$_1$ to C$_3$ alkyl", "C$_1$ to C$_6$ alkyl", (and the equivalent term "C$_1$-C$_6$ alkyl") "C$_3$ to C$_6$ alkenyl", "C$_1$ to C$_4$ alkyl", "C$_1$ to C$_4$ acyl", "C$_1$ to C$_{10}$ alkylidene", and "halo", are as defined for Formula I.

The terms "carboxy-protecting group" and "protected carboxy" as used in the application refer to one of the carboxylic acid substituents commonly employed to block or protect the carboxylic acid functionality while reacting other functional groups on the compound. Examples of such carboxylic acid protecting groups include tert-butyl, 4-methoxybenzyl, benzhydryl (diphenylmethyl), benzyl, para-nitrobenzyl, 2,4,6-trimethoxybenzyl, trityl, 4-methoxytrityl, 4,4'-dimethoxytrityl, and 4,4',4''-trimethoxytrityl and like moieties. The species of carboxy-protecting group employed is not critical so long as the derivatized carboxylic acid is stable to the condition of subsequent reaction(s) (such as alkylation) on other positions of the final products of Formula I and the intermediates of Formula II and can be removed at the appropriate point without disrupting the remainder of the molecule. Preferred carboxylic acid protecting groups include benzyl, benzhydryl (diphenylmethyl), para-nitrobenzyl and 4-methoxybenzyl, with the more preferred groups being benzhydryl and para-nitrobenzyl. Similar carboxy-protecting groups used in the heterocyclic art are similarly embraced by the above terms. Further examples of these groups are found in E. Haslam in "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

A preferred group of the intermediate compounds of Formula II occurs when:
$R_1$ is methyl;
$R_2$ is n-propyl;
$R_3$, $R_4$, $R_5$, $R_c$, and $R_d$ are each hydrogen;
Z is 0;
W is 1;
n is 0 or 1;
[Tet-L-B] is a disubstituted 1H- or 2H-tetrazolyl ring of the formula:

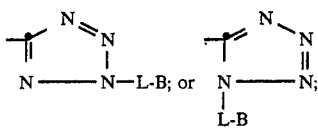

L is
(1) $C_1$ to $C_6$ alkylidene; or
(2) a group of the formula

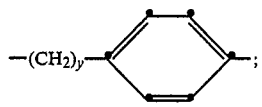

wherein y is one (and the phenyl ring is also bonded to B); and
B is cyano, bromo, or ethyl ester.

The most useful groups of intermediates occurs within the above preferred group of intermediates. The first such group has B as cyano, the second has B as the ethyl ester, and the third has B as bromo. All three groups set n equal to 1; thus the 5-position of the interior tetrazolyl ring is bonded through a methylene group to the interior phenyl ring.

The above group of cyano intermediates (B is cyano) contains two further preferred groups. One such group has the interior linking group L as straight chain $C_1$, $C_3$ or $C_4$ alkylidene [methylene, trimethylene or tetramethylene, respectively], which L group is bonded to the N-1 position of the interior tetrazolyl ring. The other preferred group of cyano intermediates occurs when either L is methylene, trimethylene, tetramethylene, pentamethylene, hexamethylene or 2,2-dimethyltetramethylene, (wherein the C-1 position of the tetramethylene group is bonded to B), or when L is a group of the formula

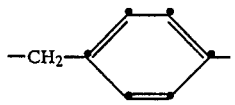

(wherein the phenyl ring is bonded to B), and L in turn is bonded at the other end to the N-2 position of the interior tetrazolyl group. This latter group of cyano intermediates contains an especially useful compound, wherein L is a straight-chain $C_3$ alkylidene (i.e., trimethylene) group.

The above (most useful) group of ethyl ester intermediates (i.e., B is the ethyl ester) also contains a preferred group of compounds. The preferred group has L as a $C_1$, $C_3$ or $C_4$ straight-chain alkylidene (i.e., methylene, trimethylene or tetramethylene) group. A more preferred group additionally has one end of such L group bonded to the N-2 position of the interior tetrazolyl ring.

The third of the above most useful groups is the bromo group of intermediates (B is bromo). In the bromo group, compounds wherein L is trimethylene, pentamethylene, or hexamethylene, are preferred, and especially so when one end of these L groups is bonded to the N-2 position of the interior tetrazole ring. Another preferred group of bromo compounds occurs when L is trimethylene which bonded at one end to the N-1 position of the interior tetrazole.

The final compounds (Formula 1) are synthesized from the instant intermediate compounds by methods well known in the art. For example, when B in Formula II is halo, the intermediate can be converted to the cyano intermediate (B=cyano) or to the final products wherein A is the amine group $-NR_fR_g$ or the thioether group $-S-R_h$. Thus, the halo intermediate can be reacted with a source of nucleophilic cyanide anion under $S_n2$ conditions. Typically, sodium or potassium cyanide (usually in excess) is reacted with the halo intermediate in a polar, aprotic solvent (such as dimethylsulfoxide or N,N-dimethylformamide) at preferably elevated temperatures (50° C. to the reflux temperature of mixture, although room temperature is also acceptable).

The halo intermediates can be converted to the mercapto final products by reacting the halo intermediate with the corresponding alkyl, phenyl or benzyl mercaptan. The reaction is carried out in a polar aprotic solvent such as dimethylsulfoxide. Heating the reaction mixture is optional. Under similar conditions the "amine" final product (A=$-NR_fR_g$) can be synthesized from the halo intermediate. The appropriate amine (or amide) $HNR_fR_g$ is combined with the halo intermediate (preferably with a large excess of amine) in an aprotic solvent such as acetonitrile at low temperatures.

The mercapto final products synthesized from the halo intermediate can be converted to the corresponding sulfoxide and sulfone (Formula I, q is 1 or 2, respectively) compounds using a mild oxidizing agent. Sodium periodate is the reagent of choice for the synthesis of the sulfoxide compound. The periodate reagent and the sulfide final product are combined in polar, usually protic solvents (such as a water/methanol mixture) and stirred at room temperature or below. Peracids are effective reagents for converting the sulfide final product to the sulfone final product. The sulfide is dissolved in an inert solvent (such as the chlorohydrocarbons, and particularly dichloromethane). The peracid, such as meta-chloroperbenzoic acid, is added slowly and the mixture stirred at ambient temperature. A slight excess of the peracid is preferably present.

The cyano intermediate of Formula II (B is cyano) can be converted to either the 5-(tetrazolyl) final product (A is 5-(tetrazolyl), as either the 1H- or 2H- isomer or a mixture) or the carboxy final products (or the salts thereof) by methods known in the art. Thus, the cyano intermediates are treated with an alkali metal azide such as sodium azide, ammonium chloride, and (optionally) lithium chloride in a non-reactive high-boiling solvent such as N,N-dimethylformamide (DMF), preferably at temperatures from about 60° C. to about 125° C. Alternatively, tri-(n-butyl)tin azide or tetramethylguanidinium azide, in a solvent such as tetrahydrofuran, dimethoxyethane, diethoxyethane, or the like, may be used in place of the alkali metal azide, ammonium chloride, lithium chloride and DMF.

As indicated above, one method of synthesizing the carboxy final product (Formula I, A=carboxy) is to hydrolyze the cyano intermediates. The hydrolysis generally involves heating the cyano derivative in aqueous alcohol in the presence of a base such as sodium or potassium hydroxide. Another method of synthesizing the carboxy final products is to hydrolyze the ester intermediate (Formula II, B is a group of the formula

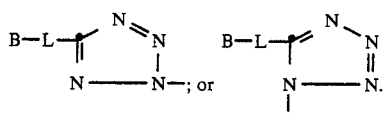

There are two major Class 1 reactions; one involves alkylating the interior tetrazole when the tetrazole is already a part of the rest of the molecule, the other involves assembling the interior linking group by combining two otherwise complete subunits (one containing the ketophenone and one containing the interior tetrazole ring.

The first Class 1 reaction, called for convenience sake the "core-tetrazole alkylation", is depicted below in Scheme 1:

Scheme 1

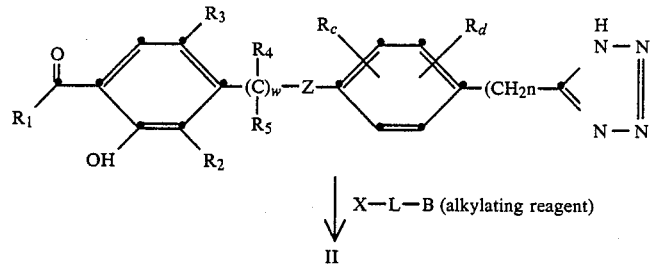

—COOR$_6$). For example, when R$_6$ is ethyl, the ethyl ester intermediate is treated with aqueous sodium or potassium hydroxide solution at a high temperature (such as 50° C. up to the reflux temperature of the mixture). The free acid final product can be isolated by acidifying (for example, with 5N hydrochloric acid) the (cooled) reaction mixture. If R$_6$ is a carboxy-protecting group, the group is removed by methods well known in the art. Thus, the benzhydryl ester can be removed by heating the ester in a strong organic acid such as trifluoroacetic acid or acetic acid. The salts of the carboxy final products are made by reacting the free acid with the appropriate base in the normal manner.

The desired products from the above reactions can be isolated by conventional means, and preferably by chromatography. Column chromatography is a preferred method, and high pressure column chromatography over silica offers a most efficient way of purifying the final products.

The intermediates of Formula II are made by a variety of methods. For convenience sake the following synthetic discussion will be divided according to the two broad types of substitution pattern of the interior tetrazole. Thus, the first class of reactions ("Class 1 reactions") synthesize intermediates wherein [Tet] (the interior tetrazole) is bonded to the interior linking group at the 5 position and is of the formula:

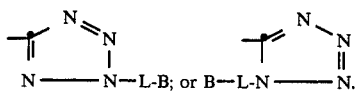

The second class of reactions ("Class 2") synthesizes intermediates where [Tet] has the opposite configuration and is of the formula:

In the above Scheme, R$_1$ through R$_5$, R$_c$, R$_d$, Z, B, L, w and n are as for Formula II. "X" is a good leaving group for S$_n$2 reactions, and is preferably chloro or bromo. (Note that the tetrazole of the starting material can also be 2-H isomer, or alkali metal salt of either the 1H- or 2H-isomer.)

The reaction depicted in the above Scheme usually involves approximately equimolar amounts of the starting material and reagent, although other ratios, especially those wherein the alkylating reagent is in excess, are operative. The reaction is best carried out in a polar, aprotic solvent employing an alkali metal salt of the tetrazole starting material, or in the presence of a base, such as an alkali metal hydroxide. Preferred reaction conditions involve employing the sodium salt of monosubstituted tetrazole (4) in either dimethylformamide or tetrahydrofuran, along with potassium carbonate in a solvent such as acetone or methyl ethyl ketone, or in a mixture of acetonitrile and hexamethylphosphoramide. When the leaving group is bromo, a catalytic amount of an iodide salt, such as potassium iodide, may be added to speed the reaction. The temperature of the reaction is from about ambient temperature to about the reflux temperature of the reaction mixture. When elevated temperatures are employed, the reaction is usually complete in 1–4 hours.

The core tetrazole alkylation depicted in Scheme 1 affords both the N-1 and N-2 (interior) tetrazole isomers of the intermediates. These isomers may be separated by standard techniques at any of the intermediate stages or upon formation of the final products. Such techniques include fractional crystallization or preferably column chromatographic techniques, such as high pressure liquid chromatography.

The second of the two Class 1 reactions is depicted below as Scheme 2:

Scheme 2

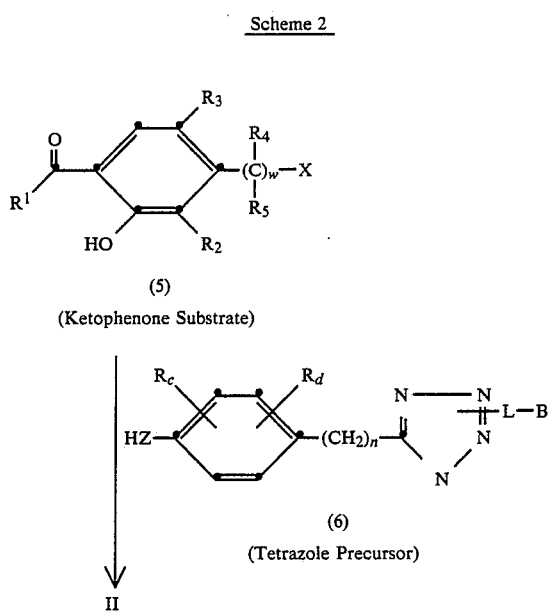

In the above Scheme, the variables $R_1$ through $R_5$, $R_c$, $R_d$, w, Z, n, and L are the same as for Formula II. B is either cyano or a group of the formula —$COOR_6$. Finally, X is a good leaving group for $S_n2$ conditions, and is especially a chloro or bromo group.

The reaction depicted in Scheme II above usually employs equimolar amounts of the Ketophenone Substrate and Tetrazole Precursor, although different stoichiometries are completely operative. The reaction is best carried out in nonreactive solvents such as ketones, especially acetone or methyl ethyl ketone, or in dimethylformamide, and in the presence of a base (preferably an alkali metal hydroxide or carbonate, and more preferably potassium carbonate). Especially when X is chloro, a catalyst such as potassium or sodium iodide may be added to increase the reaction rate. Alternatively, ethanol and one equivalent of sodium hydroxide per equivalent of Tetrazole Precursor could be a reaction medium for Scheme 2. The reaction may be carried out at temperatures of about ambient temperature up to the boiling point of the reaction mixture, the former being preferred.

The two major types of Class 2 Reactions (i.e., the reaction products possess interior tetrazoles bonded to the interior linking group through the N-1 or N-2 position) are set forth below as Schemes 3 and 4.

The first such reaction alkylates the interior tetrazole with the rest of the interior linking group (bonded to the ketophenone). This interior tetrazole alkylation is depicted below as Scheme 3:

Scheme 3

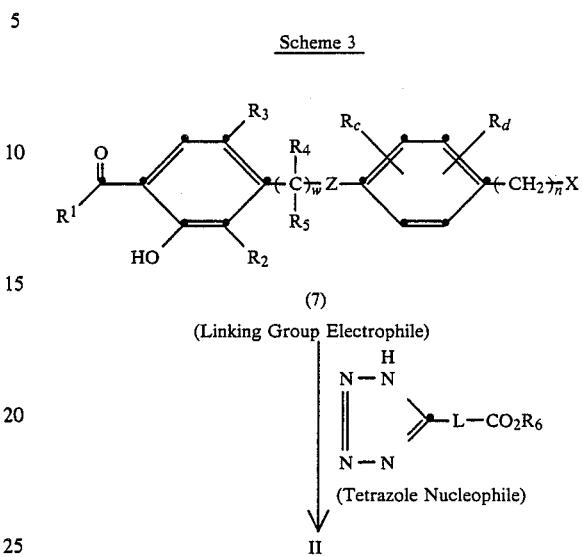

In the above Scheme 3 both the N-1 and N-2 isomers of the interior tetrazole are produced. The variable n is one to six, while all other variables used that are a part of Formula II have the same meaning as Formula II. "X" on the Linking Group Electrophile is a good $S_n2$ leaving group, and is preferably chloro or bromo.

The alkylation of Scheme 3 can employ equimolar amounts of the Linking Group Electrophile and Tetrazole Nucleophile, although the reaction is operative using excesses of either compound. The reaction uses aprotic, polar solvents such as ketones (acetone, methylethylketone), and preferably methylethylketone. A weak base (such as sodium or potassium carbonate.) is added in at least an equimolar amount of the Tetrazole Nucleophile in order to convert the tetrazole to the anionic form in situ. When the leaving group X is bromo, a catalytic amount of potassium or sodium iodide is preferably added. The reaction is carried out from about 25° C. to the reflux temperature of the mixture The reaction is typically complete in two hours. The isomers of the tetrazole product are preferably separated by column chromatography over silica, and more preferably with high pressure liquid chromatography, diluted with a gradient of ethyl acetate in hexane plus 1% acetic acid or methanol in methylene chloride.

The second of the Class II reactions is a three-part sequence of an amine acylation, the dehydration of the resultant amide to the imino chloride, followed by the cyclization of the imino chloride to the tetrazole. This reaction sequence is depicted below as Scheme 4.

Scheme 4

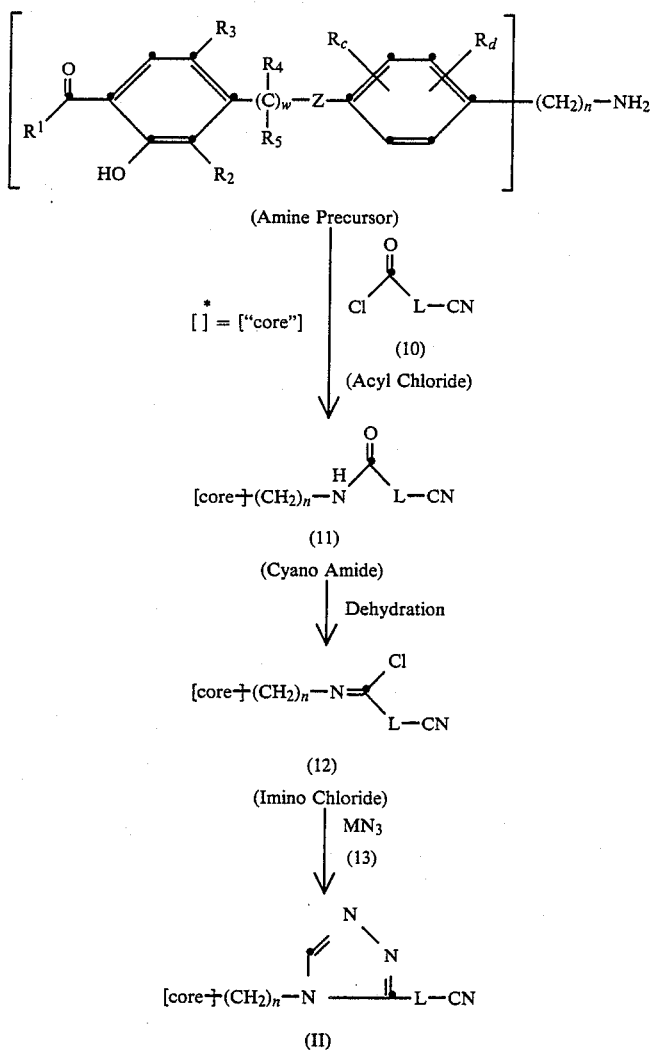

[ ] = ["core"]

(Amine Precursor)

(10) (Acyl Chloride)

(11) (Cyano Amide)

Dehydration

(12) (Imino Chloride)

MN₃ (13)

(II)

In the above Scheme, only intermediates wherein the interior link is bonded to N-1 position are produced. All variables used above that are also used in conjunction with the intermediates of Formula II are as defined for Formula II.

The amine acylation reaction above is carried out under standard Schotten-Baumann conditions (i.e., aqueous alkaline conditions). The reaction uses preferably an approximately equimolar amount of Amine Precursor and Acyl Chloride. The Acyl Chloride is usually formed immediately before the reaction from the acid by standard methods and used without further purification). The reaction temperature is usually about 0° C. The reaction is usually complete in about 4 hours. The product is usually isolated by high p-essure liquid chromatography over silica gel eluted with toluene/ethyl acetate.

The resultant cyano amide is dehydrated with either thionyl chloride or phosgene in the presence of a sequestering base such as pyridine to give the imino chloride. Again, equimolar amounts of Cyano Amide and SOCl₂ or COCl₂ is usually used. The reaction is preferably carried out in a dry, inert atmosphere. The solvent is generally a highly polar, aprotic one such as an ether (for example, diethyl ether or dimethoxyethane). The reaction is stirred at 0° C. to abo t room temperature. The resultant imino chloride is used without further purification.

The final reaction in the above scheme uses an alkali metal azide to effect cyclization of the imino chloride to a tetrazole. The reactio- conditions for this reaction are those of the conversion of the cyano intermediates of Formula II (B=cyano) to the tetrazole final products of Formula I (A=(5-tetrazolyl)).

Many of the reagents and starting materials in the above Schemes 1 through 4 are known in the art, and some are also commercially available. For example, many of the various precursors, starting materials and reagents are discussed in Marshall et al., U.S. Pat. No. 4,661,505, issued April 28, 1987, Goldsworthy et al., U.S. Pat. No. 4,595,540, issued June 17, 1986, R. D. Dillard EPO Patent Application Publication No. 132,366, published Jan. 30, 1985 and EPO Patent Application Publication Nos. 28,063; 110,541; 132,124; and 146,333, all of which are herein incorporated by reference.

More specifically, the Tetrazole Nucleophile precursor of Scheme 2 above can be synthesized in the manner set forth in Scheme 5:

Scheme 6). The synthesis of the precursor of Formula IV is set forth below in Scheme 6:

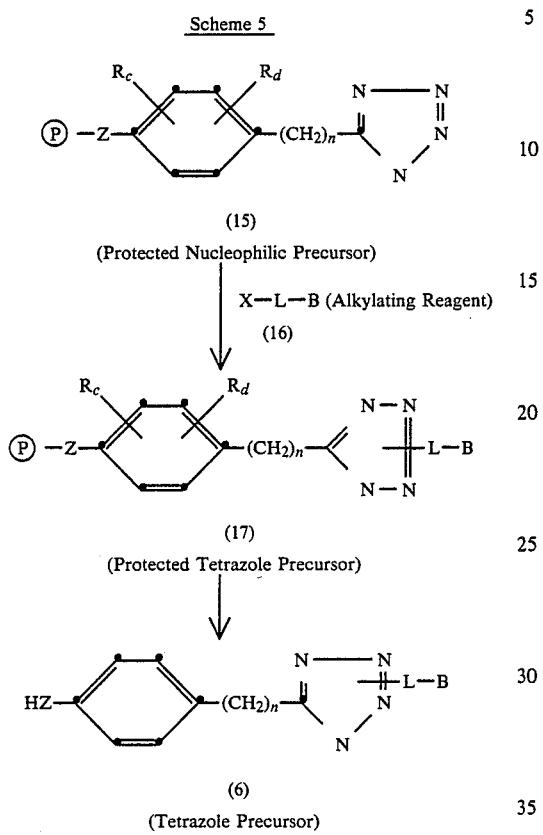

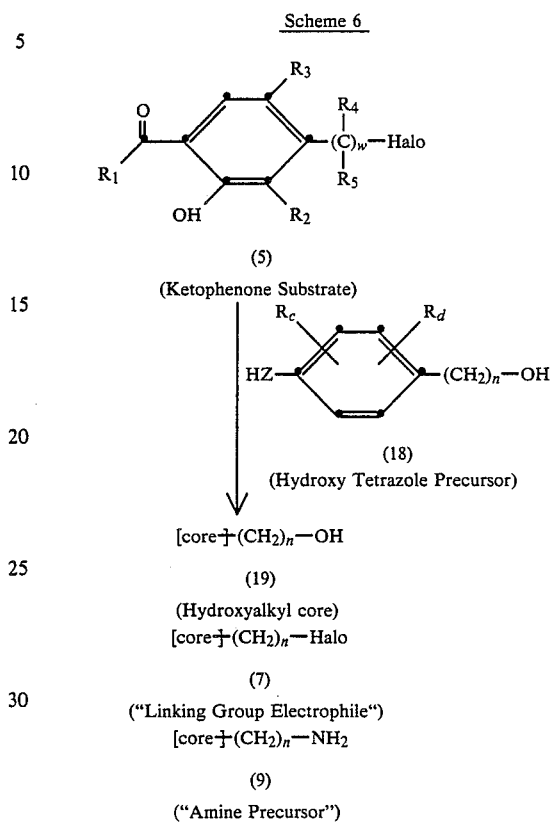

In the above Scheme Z, $R_c$, $R_d$, n, L and B are as described for Formula II. X is a good leaving group such as chloro or bromo, and P is a hydroxy, mercaptan or amino protecting group, as required.

The first reaction in Scheme 5 is an alkylation of the tetrazole, producing a mixture of N-1 and N-2 isomers of the protected Tetrazole Nucleophile. The hydroxy, mercaptan or amino protecting group is then removed to give the required Nucleophilic Tetrazole. The various protecting groups and the methods for their removal and placement are known in the art and are found in standard works such as T. W. Greene, "Protective Groups in Organic Synthesis", John Wiley and Sons, New York, 1981.

The larger precursors for the Class II reactions can also be made by methods well known in the art. Both the Reactions of Scheme 3 and Scheme 4 employ a precursor of the following general Formula IV In Scheme 6, the variables in both the Ketophenone Substrate and the Hydroxyalkyl Tetrazole Precursor are as defined for Scheme 2. Furthermore, the Hydroxyalkyl Core is synthesized according to the reaction conditions set forth in Scheme 2. Of course, some undesirable side product will result from alkylation on the "wrong" hydroxy group, i.e., the hydroxy of the $-(CH_2)_n-$ group. The conversions of the hydroxy group the halo group and of the halo group to the primary amine group are done by methods well known in the art (such as the Gabriel synthesis).

Scheme 7 below sets forth below the synthesis for the Tetrazole Nucleophile of Scheme 3.

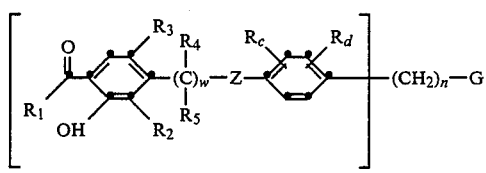

IV wherein all the variables but G are as described in Schemes 3 and 4, and G is chloro, bromo or amino. (The part of the molecule of IV encompassed by brackets will be represented by the symbol ["core"] below in Scheme 7

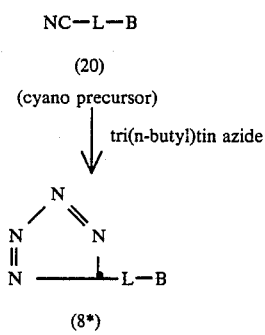

In Scheme 7, L is as defined for Formula II and B is either a group of the formula —COOR$_6$ or is cyano. The above reaction employs the same conditions as the analogous reaction converting the cyano intermediates of Formula II to the tetrazole final products (A=5-(tetrazolyl) of Formula I. (When B above is also cyano, a large amount of the cyano precursor is used in relation to the tin azide reagent.)

The compounds of Formula I should be useful in treating any condition, including clinical conditions, which is characterized by excessive release of leukotrienes C$_4$, D$_4$, or E$_4$. These conditions include immediate type hypersensitivity reactions such as asthma. Evidence obtained over the past few years has shown the presence of leukotrienes in sputum of patients with chronic bronchitis (Turnbull, et al., Lancet II, 526 (1977)) and cystic fibrosis (Cromwell, et al., Lancet II, 164 (1981)), suggesting a role of leukotrienes in the pathology of those diseases. Furthermore, Lewis and colleagues [Int. J. Immunopharmacology, 4, 85 (1982)] have recently detected material in rheumatoid synovial fluid that reacts antigenically with antibody to LTD$_4$. This may hallmark the existence of leukotriene permeability factors that, together with LTB$_4$, augment the inflammatory process in the diseased joints. Therefore, the compounds described in this invention should also alleviate some of the symptoms of chronic bronchitis and cystic fibrosis and possibly rheumatoid arthritis by virtue of their ability to antagonize leukotrienes. The compounds are also useful for inhibiting the cardiovascular effects of leukotrienes thereby rendering them useful for treating conditions such as shock and ischemic heart disease.

The term "excessive release" of leukotrienes refers to an amount of leukotrienes sufficient to cause the particular condition associated with such amount. The amount of leukotriene which is considered to be excessive will depend on a variety of factors, including the specific leukotriene(s) involved, the amount of leukotriene required to cause the particular condition, and the species of the mammal involved. As will be appreciated by those skilled in the art, the success of treating a mammal suffering from or suscetible to a condition characterized by an excessive release of leukotrienes with a compound of Formula I will be measured by the regression or prevention of the symptoms of the condition. The compounds of Formula I provide exceptionally high blood levels.

Leukotriene antaqonism of the claimed final products was demonstrated by the following test procedure:

Male, Hartley guinea pigs weighing 200–450 grams were killed by decapitation. A section of terminal ileum was removed, the lumen cleaned, and the tissue divided into 2.5 cm. segments. The ilea were mounted in 10 ml. tissue baths containing Krebs-bicarbonate solution of the following composition in mmoles/liter: KCl, 4.6; CaCl$_2$·2H$_2$O, 1.2; KH$_2$PO$_4$, 1.2; MgSO$_4$·7H20, 1.2; NaCl, 118.2; NaHCO$_3$, 24.8; and dextrose, 10.0. The bath fluid was maintained at 37° C. and aerated with 95 percent oxygen and 5 percent CO$_2$. In addition, the buffer contained $1 \times 10^{+6}$ $\underline{M}$ atropine to reduce ileal spontaneous activity. Isometric measurements were made with a Grass FTO3C force-displacement transducer and recorded on a Grass polygraph as change in grams of force. A passive force of 0.5 g. was applied to the tissues. After an appropriate equilibration period, single submaximal control responses to pure LTD$_4$ were obtained. Following a five minute exposure of the ileum to an experimental drug, the control concentration of LTD$_4$ was added to the tissue bath. The response of the ileum to LTD$_4$ in the presence of the drug was compared to the response in the absence of the drug. Various degrees of LTD$_4$ antagonism were obtained using 2–4 different concentrations of an experimental compound on a single ileum. The antagonist concentration that produced 50% inhibition of the LTD$_4$ responses ($-\log IC_{50}$) was interpolated from these data using linear regression.

For some of the drugs in this series a more detailed analysis of LTD$_4$ antagonism was made. In these experiments, cumulative concentration-response curves were obtained to LTD$_4$ in guinea pig ileum and trachea. This was followed by a 30 minute incubation with various concentrations of the experimental drug. The concentration response curve to LTD$_4$ was then repeated in the presence of the antagonist. Only one concentration of antagonist was used on a single tissue. K$_B$ values were calculated by the method of Furthgott [Ann. N.Y. Acad. Sci., 139, 553 (1967)] using the following equation.

$$K_B = \frac{[\text{Antagonist}]}{\text{Dose Ratio} - 1}$$

Dose ratio refers to the concentration of agonist required to elicit 50 percent of the maximal response (ED$_{50}$) in the presence of the antagonist divided by the ED$_{50}$ in the absence of the antagonist. Calculations were performed with the aid of a computer and a diqital plotter. The negative log of the dissociation K$_B$ ("pK$_B$") is given for some of the compounds in the table below.

The testing of the compounds of Formula I in these two procedures is summarized in Table I.

TABLE I

| Percent inhibition of LTD$_4$ evoked ileal contractions | | |
|---|---|---|
| Example No. | $-\log IC_{50}$ | pK$_B$ |
| 15 | — | 6.65 |
| 16 |   | 6.01 |
| 17 | — | 6.45 |
| 21 | 7.76 | — |
| 22 | 7.93 | — |
| 23 | 7.85 | — |
| 24 | 8.42 |   |
| 25 | 7.72 | — |
| 26 | 8.09 | — |
| 27 | — | 7.38 |
| 28 | — | 7.70 |
| 29 | — | 7.64 |
| 31 | 7.55 | — |
| 32 | 7.24 | — |
| 33 | 7.70 | — |
| 34 | 7.26 | — |

TABLE I-continued

| Percent inhibition of LTD$_4$ evoked ileal contractions | | |
|---|---|---|
| Example No. | −log IC$_{50}$ | pK$_B$ |
| 35 | 7.93 | — |
| 36 | — | 7.63 |
| 37 | — | 6.37 |
| 38 | — | 7.90 |
| 39 | — | 6.50 |
| 40 | — | 6.37 |

The compounds or formulations of the present invention may be administered by the oral and rectal routes, topically, parenterally, for example, by injection and by continuous or discontinuous intra-arterial infusion, in the form of, for example, tablets, lozenges, sublingual tablets, sachets, cachets, elixirs, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to 500 mg. (from about 5 to 50 mg. in the case of parenteral or inhalation administration, and from about 25 to 500 mg. in the case of oral or rectal administration) of a compound of Formula I. Therapeutically-effective, and thus leukotriene-antagonizing, dosages of from about 0.5 to 300 mg./kg. per day, preferably 0.5 to 20 mg./kg., of the compound of Formula I be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The pharmaceutical formulations of the present invention normally will consist of at least one compound of Formula I mixed with a carrier, or diluted by a carrier, or enclosed or encapsulated by an ingestible carrier in the form of a capsule, sachet, cachet, paper or other container or by a disposable container such as an ampoule. A carrier (or diluent) may be a solid, semi-solid or liquid material which serves as a vehicle, excipient or medium for the active therapeutic substance.

Some examples of the pharmaceutically-acceptable carriers which may be employed in the pharmaceutical formulation of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical formulations of the present invention are capsules, tablets, suppositories, injectable solutions, creams and ointments. Especially preferred are formulations for inhalation application, such as an aerosol, for oral ingestion and solutions for intravenous injection.

A preferred pharmaceutical invention of the instant invention comprises a therapeutically-effective amount of the preferred compounds of Formula I and a pharmaceutically-acceptable carrier, with the most preferred formulations comprising a therapeutically-effective amount of the compound of Example 24 (or a pharmaceutically-acceptable base-addition salt thereof) or the sodium salt of the compound of Example 24 and a pharmaceutically-acceptable carrier.

Preferred methods of treating a mammal suffering from or susceptible to any condition characterized by an excessive release of leukotrienes C$_4$, D$_4$, and E$_4$, which comprises administering to said mammal a leukotriene antagonizing amount of the compound of Example 24 (or a pharmaceutically-acceptable salt thereof), the sodium salt of the compound of Example 24, or a compound of the preferred compounds of claim 1.

The following Examples and Preparations are provided merely to further illustrate the invention. The scope of the inventon is not to be construed as merely consisting of the following Examples.

In the following Examples and Preparations, melting point, nuclear magnetic resonance spectra, high pressure liquid chromatography, ethyl acetate, N,N-dimethylformamide, methylethylketone, 1,2-dimethoxyethane and hexamethylphosphoramide are abbreviated m.p., n.m.r., HPLC, EA, DMF, MEK, DME, and HMPA, respectively. (The reported melting points are uncorrected).

Nuclear Magnetic Resonance spectra were obtained on a General Electric Model QE-300 300 MHz instrument or a Bruker 270 MHz instrument. HPLC were obtained on a Waters Associates Prep 500 ® Preparatory Scale HPLC equipped with PREPPAK ® 500 silica columns.

EXAMPLE 1

Ethyl 5-[(4-((4-acetyl-3-hydroxy-2-propylphenyl)methoxy)phenyl)methyl]-2H-tetrazole-2-(5-valeroate) and the corresponding 1H-tetrazole-1-isomer 1-[2-Hydroxy-3-propyl-4-((4-(1H-tetrazol-5-ylmethyl)phenoxy)methyl)phenyl]ethanone sodium salt (15.0 g, 0.038 mol) was dissolved in DMF (150 ml). Ethyl 5-bromovalerate (22.99 g, 0.11 mol) was added and the solution was stirred at room temperature for 2 days. The reaction mixture was poured into water and extracted (3×) with ethyl acetate. The ethyl acetate extract was washed with brine and dried over sodium sulfate. The filtrate was concentrated in vacuo and the concentrate was chromatographed by HPLC on a silica gel column eluted isocratically with a 9:1 toluene:ethyl acetate mixture to yield the 2H-tetrazole-2-isomer in an 11.8 g yield. The eluting solvent was then changed to a 7:3 toluene:ethyl acetate mixture and the 1H-tetrazole-1-isomer was obtained in a 4.0 g yield. The 2H-tetrazole-2-isomer had the following properties: n.m.r. (300 MHz, CDCl$_3$) δ: 1.0 (t, 3H); 1.24 (t, 3H); 1.6 (m, 4H); 2.04 (m, 2H); 2.36 (t, 2H); 2.6 (s, 3H); 2.61 (m, 2H);

4.13 (q, 2H); 4.2 (s, 2H); 4.6 (t, 2H); 5.08 (s, 2H); 6.9 (d, 2H); 7.0 (d, 1H); 7.25 (d, 2H); 7.6 (d, 1H); 12.66 (s, 1H).

Analysis Calculated for $C_{27}H_{35}N_4O_5$: Theory: C, 65.57; H, 6.93; N, 11.33; Found: C, 65.64; H, 6.92; N, 11.54.

The 1H-tetrazole-1-isomer had the following properties: n.m.r. (300 MHz, CDCl$_3$) δ: 1.0 (t, 3H); 1.24 (t, 3H); 1.6 (m, 4H); 1.8 (m, 2H); 2.25 (t, 2H); 2.64 (s, 3H); 2.7 (m, 2H); 4.12 (m, 4H); 4.24 (s, 2H); 5.08 (s, 2H); 6.91 (d, 2H); 7.0 (d, 1H); 7.14 (d, 2H); 7.62 (d, 2H); 12.66 (s, 1H).

Analysis Calculated for $C_{27}H_{34}N_4O_5$: Theory: C, 65.57; H, 6.93; N, 11.33; Found: C, 65.77; H, 7.03; N, 11.31.

EXAMPLE 2

Ethyl 5-[(4-((4-Acetyl-3-hydroxy-2-propylphenyl)-methoxy)phenyl)methyl]-2H-tetrazole-2-(4-butyrate) and the corresponding 1H-tetrazole-1-isomer In a procedure similar to that of Example 1, the following reagents and amounts were combined:
1-[2-Hydroxy-3-propyl-4-((4-(1H-tetrazol-5-ylmethyl)-phenoxy)methyl)phenyl]ethanone sodium salt (15.0 g, 0.38 mol);
Ethyl 4-Bromobutyrate (21.4 g, 0.11 mol); and
DMF (150 ml).

Isolation of the crude product and chromatography were done in the usual manner yielded 11.2 g
of the 2H-tetrazole-2-isomer: (300 MHz, CDCl$_3$) δ: 1.0 (t, 3H); 1.25 (t, 3H); 1.6 (m, 2H); 2.35 (m, 4H); 2.63 (s, 3H); 2.7 (m, 2H); 4.13 (q, 2H); 4.18 (s, 2H); 4.64 (t, 2H); 5.06 (s, 2H); 6.9 (d, 2H); 7.0 (d, 1H); 7.15 (d, 2H); 7.6 (d, 1H); 12.66 (s, 1H).

Analysis Calculated for $C_{26}H_{32}N_4O_5$: Theory: C, 64.98; H, 6.71; N, 11.66; Found: C, 65.13; H, 6.63; N, 11.50.

Chromatography also yielded 4.8 g of the 1H-tetrazole-1-isomer: n.m.r. (300 MHz, CDCl$_3$) δ: 1.0 (t, 3H); 1.26 (t, 3H); 1.6 (m, 2H); 2.06 (m, 2H); 2.32 (t, 2H); 2.62 (s, 3H); 2.64 (m, 2H); 4.14 (q, 2H); 4.26 (m, 4H); 5.08 (s, 2H); 6.92 (d, 2H); 7.0 (d, 1H); 7.16 (d, 2H); 7.6 (d, 1H); 12.66 (s, 1H).

Analysis Calculated for $C_{26}H_{32}N_4O_5$: Theory: C, 64.98; H, 6.71; N, 11.66; Found: C, 64.91; H, 6.74; N, 11.61.

EXAMPLE 3

Ethyl 5-[(4-((4-Acetyl-3-hydroxy-2-propylphenyl)-methoxy)phenyl)methyl]-2H-tetrazole-2-(2-acetate) and the corresponding 1H-tetrazole-1-isomer In a procedure similar to that of Example 2, the following reagents and amounts were combined:
1-[2-Hydroxy-3-propyl-4-((4-(1H-tetrazol-5-ylmethyl)-phenoxy)phenyl]ethanone sodium salt (15.0 g, 0.38 mol);
Ethyl 2-Bromoacetate (19.4 g, 0.11 mol); and
DMF (150 ml).

The usual work-up and chromatography yielded 8.2 g of the 2H-tetrazole-2-isomer: n.m.r. (270 MHz, CDCl$_3$) δ: 1.0 (t, 3H); 1.31 (t, 3H); 1.6 (m, 2H); 2.6 (s, 3H); 2.64 (m, 2H); 4.24 (s, 2H); 4.26 (q, 2H); 5.05 (s, 2H); 5.35 (s, 2H); 6.88 (d, 2H); 7.0 (d, 1H); 7.23 (d, 2H); 7.58 (d, 1H); 12.66 (s, 1H).

Analysis Calculated for $C_{24}H_{28}N_4O_5$: Theory: C, 63.70; H, 6.24; N, 12.38; Found: C, 61.91; H, 6.23; N, 11.97.

Chromatography also yielded 8.2 g of the 1H-tetrazole isomer: m.p.: 105° C; n.m.r. (270 MHz, CDCl$_3$) δ: 0.9 (t, 3H); 1.12 (t, 3H); 1.5 (m, 2H); 2.63 (s, 5H); 4.05 (q, 2H); 4.26 (s, 2H); 5.12 (s, 2H); 5.5 (s, 2H); 6.95 (d, 2H); 7.04 (d, 1H); 7.2 (d, 2H); 7.8 (d, 1H); 12.7 (s, 1H).

Analysis Calculated for $C_{26}H_{32}H_4O_5$: Theory: C, 63.70; H, 6.24; N, 12.38; Found: C, 63.50; H, 5.96; N, 12.39.

EXAMPLE 4

5-[(4-((4-Acetyl-3-hydroxy-2-propylphenyl)methoxy)-phenyl)methyl]-2H-tetrazole-2-acetonitrile and the corresponding 1H-tetrazole-1-analog 1-[2-Hydroxy-3-propyl-4-((4-(1H-tetrazol-5-ylmethyl)phenoxy)methyl)phenyl]ethanone sodium salt (17.3 g, 0.045 mmol) was added to THF (200 ml). After stirring for 5 minutes, the mixture gelled. 0.5N Sodium hydroxide (1-2 ml) was added and the gel dissolved. 2-Bromoacetonitrile was added (6 g, 0.5 mol, 3.5 ml) and the reaction solution was heated to reflux temperature and stirred for 3 hours. The resultant precipitate was collected by filtration and the filtrate was reduced in vacuo. The residue was dissolved in ethyl acetate. The ethyl acetate solution was washed with water and brine, dried over sodium sulfate, filtered, and the filtrate was taken to dryness and in vacuo. The resultant residue was chromatographed by HPLC on a silica gel column, eluted first with toluene then a 9:1 toluene-:ethyl acetate mixture after the forerunning compound had been eluted. The yield of the 2H-tetrazole-2-isomer compound was 6.9 g: m.p. 101-103° C; n.m.r. (300 MHz, CDCl$_3$) δ: 1.0 (t, 3H); 1.6 (q, 2H); 2.6 (s, 3H); 2.7 (t, 2H); 4.2 s, 2H); 5.1 (s, 2H); 5.5 (s, 2H); 6.9 (d, 2H); 7.0 (d, 1H); 7.25 (d, 2H); 7.6 (d, 1H); 12.7 (s, 1H).

Analysis Calculated for $C_{22}H_{23}N_5O_3$: Theory: C, 65.17; H, 5.72; N, 17.27; Found: C, 65.61; H, 5.56; N, 17.16.

The yield of the 1H-tetrazole-1-isomer was 8.6 g; m.p. 89°–92° C.; n.m.r. (300 MHz, CDCl$_3$) δ: 1.0 (t, 3H); 1.6 (q, 2H); 2.65 (s, 3H); 2.7 (t, 2H); 4.4 (s, 2H); 5.0 (s, 2H); 5.1 (s, 2H); 7.0 (d+d, 3H); 7.2 (d, 2H); 7.6 (d, 2H); 12.7 (s, 1H).

Analysis Calculated for $C_{22}H_{23}N_5O_5$: Theory: C, 65.17; H, 5.72; N, 17.27; Found: C, 65.34; H, 5.83; N, 17.02.

EXAMPLE 5

5-[(4-((4-Acetyl-3-hydroxy-2-propylphenyl)methoxy)-phenyl)methyl]-2-(3-bromopropyl)-2H-tetrazole and the corresponding 1-isomer 1-[2-Hydroxy-3-propyl-4-((4-(1H-tetrazol-5-ylmethyl)phenoxy)methyl)phenyl]ethanone sodium salt (15 g, 0.039 mol) was added to THF (150 ml) and the minimum amount of 1N sodium hydroxide soluton was added to effect solution. 1,3-Dibromopropane (12.12 g, 0.06 mol) was added and the reaction solution was stirred at room temperature for 24 hours. The reaction mixuture was concentrated in vacuo. Water was added to the concentrate and the resultant mixture was extracted with ethyl acetate (3×). The organic layers were combined, washed with water, dried over sodium sulfate, filtered, and concentrated. The resultant residue was chromatographed by HPLC on a silica gel column eluted with a mixture of 9:1 toluene:ethyl acetate to yield 3.0 g of a light yellow oil of the 2H-tetrazole-2-isomer of the above product.

Analysis Calculated for $C_{23}H_{25}N_4O_3Br$: Theory: C, 56.68; H, 5.58; N, 11.50; Found: C, 56.84; H, 5.77; N, 11.59.

n.m.r. (300 MHz, CDCl₃) δ: 1.0 (t, 3H); 1.6 (q, 2H); 2.5 (q, 2H); 2.6 (s, 3H); 2.65 (t, 2H); 3.4 (t, 2H); 4.2 (s, 2H); 4.75 (t, 2H); 5.15 (s, 2H); 6.9 (d, 2H); 7.0 (d, 1H); 7.3 (d, 2H); 7.6 (d, 1H); 12.7 (s, 1H).

The chromatography also yielded 2.0 g of the 1H-tetrazole-1-isomer: n.m.r. (300 MHz, CDCl₃) δ:1.0 (t, 3H); 1.6 (q, 2H); 2.3 (q, 3H); 2.6 (s, 3H); 2.6 (t, 2H); 3.3 (t, 3H); 4.3 (s, 2H, t, 2H); 5.1 (s, 2H); 6.9 (d, 2H); 7.0 (d, 1H); 7.15 (d, 2H); 7.6 (d, 1H); 12.7 (s, 1H).

Analysis Calculated for C₂₃H₂₅N₄O₃Br: Theory: C, 56.68; H, 5.58; N, 11.50; Found: C, 58.60; H, S.91; N, 11.93.

EXAMPLE 6

5-[(4-((4 TM Acetyl-3-hydroxy-2-propylphenyl)methoxy)phenyl)methyl]-2H-tetrazole-2-(4-butyronitrile) and the corresponding 1-isomer.

In a procedure similar to that of Example 4, 1-[2-hydroxy-3-propyl-4-((4-(1H-tetrazol-5-ylmethyl)phenoxy)methyl)phenyl]ethanone sodium salt (17.3 g, 0.045 mol) was dissolved in THF (200 ml) then 0.5N sodium hydroxide (1 ml) was added. 4-Bromobutyronitrile (7.4 g, 0.05 mol) was added and the reaction mixture was stirred at reflux temperature overnight. The reaction mixture was filtered, and the filtrate was concentrated in vacuo. The residue was dissolved in ethyl acetate and the solution was washed with water then dried over sodium sulfate, filtered and concentrated in vacuo. The residue was chromatographed by HPLC on a silica gel column eluted with a gradient of toluene to 8:2 toluene: ethyl acetate to yield 9.9 g of the 2H-tetrazole-2-isomer: m.p. 82°-84° C.; n.m.r. (300 MHz, CDCl₃) δ: 1.0 (t 3H); 1.6 (q, 2H); 2.% (m, 2H); 2 5 (m, 2H); 2.6 (s, 3H); 2.7 (t, 2H); 4.2 (s, 2H); 4.7 (t, 2H); 5.1 (s, 2H); 6.9 (d, 2H); 7.0 (d, 1H); 7.3 (d, 2H); 7.6 (d, 1H); 12.7 (s, 1H).

Analysis Calculated for C₂₄H₂₇N₅O₃: Theory: C, 66.50; H, 6.28; N, 16.16; Found: C, 66.76; H, 6.41; N, 16.29.

The chromatography also yielded 6.2 g of the 1H-tetrazole-1-isomer as an oil: n.m.r. (300 MHz, CDCl₃) δ: 1.0 (t, 3H); 1.6 (q, 2H); 2.1 (m, 2H); 2.4 (t, 2H); 2.65 (s, 3H); 2.7 (q, 2H); 4.25 (t, 2H); 4.3 (s, 2H); 5.1 (s, 2H); 6.9 (d, 2H); 7.0 (d, 1H); 7.1 (d, 2H); 7.6 (d, 1H); 12.7 (s, 1H).

Analysis Calculated for C₂₄H₂₇N₅O₃: Theory: C, 66.50; H, 6.28; N, 16.16; Found: C, 67.12; H, 6.28; N, 15.75.

EXAMPLE 7

5-[4-((4-Acetyl-3-hydroxy-2-propylphenyl)methoxy)phenyl]-2H-tetrazole-2-(4-butyronitrile)

1-2-Hydroxy-3-propyl-4-[[4-(1H-tetrazol-5-yl)phenoxy)methyl]phenyl]ethanone (10 g, 0.026 mol) was added to acetone (100 ml) and an excees of potassium carbonate (solid) was added. The reaction mixture was stirred for 30 minutes followed by the addition of 4-bromobutyronitrile (4.4 g, 0.03 mol). The resultant reaction mixture was stirred overnight at room temperature. Water was added and the mixture was extracted with ethyl acetate. The ethyl acetate extract was washed with water, dried over sodium sulfate, filtered and concentrated in vacuo. The residue was chromatographed on HPLC using the silica gel column eluted with a mixture of 9:1 toluene:ethyl acetate. This procedure yielded the title product: m.p. 108°–110° C₁ n.m.r. (300 MHz, CDCl₃) δ: 1.0 (t, 3H); 1.6 (m, 2H); 2.4-2.6 (m, 4H); 2.6 (s, 3H); 2.7 (t, 2H); 4.8 (t, 2H); 5.2 (s, 2H); 7.0 (m, 3H); 7.6 (d, 1H); 8.1 (d, 2H); 12.7 (s, 1H).

Analysis Calculated for C₂₃H₂₅N₅O₃: Theory: C, 65.86; H, 6.01; N, 16.70; Found: C, 66.16; H, 6.27; N, 16.05.

EXAMPLE 8

5-[(4-((4-acetyl-3-hydroxy-2-propylphenyl)methoxy)phenyl)methyl]-2H-tetrazole-2-(5-valeronitrile) and the corresponding 1H-tetrazole-1-isomer In a procedure similar to that of Example 6, the following reagents and amounts were combined:
1-[2-hydroxy-3-propyl-4-((4-(1H-tetrazol-5-ylmethyl)phenoxy)methyl)phenyl]ethanone sodium salt (17.3 g, 0.045 mol);
THF (200 ml);
0.5N sodium hydroxide solution (1 ml); and After the usual work-up, the residue was chromatographed by HPLC on a silica gel column eluted with a gradient of neat toluene to a mixture of 7:3 toluene:ethyl acetate to yield the 2H-tetrazole-2-isomer as an oil (9.5 g): n.m.r. (300 MHz, CDCl₃) δ: 1.0 (t, 3H); 1.6-1.8 (m, 6H); 2.2 (q, 2H); 2.4 (t, 2H); 2.6 (s, 3H); 2.7 (t, 2H); 4.2 (s, 2H); 4.6 (t, 2H); 5.1 (s, 2H); 6.9 (d, 2H); 7.0 (d, 1H); 7.2 (d, 2H); 7.4 (d, 1H); 12.7 (s, 1H).

Analysis Calculated for C₂₅H₂₉N₅O₃: Theory: C, 67.09; H, 6.53; N, 15.65; Found: C, 67.32; H, 6.48; N, 15.68.

The 1H-tetrazole-1-isomer was obtained as an oil (6.7): n.m.r. (300 MHz, CDCl₃) δ: 1.0 (t, 3H); 1.5–1.7 (m, 6H); 1.9 (q, 2H); 2.3 (t, 2H); 2.65 (s, 3H); 2.7 (t, 2H); 4.1 (t, 2H); 4.3 (s, 2H); 5.1 (s, 2H); 6.9 (d, 2H); 7.0 (d, 1H); 7.1 (d, 2H); 7.6 (d, 1H); 12.7 (s, 1H).

Analysis Calculated for C₂₅H₂₉N₅O₃: Theory: C, 67.09; H, 6.53; N, 15.65; Found: C, 67.28; H, 6.79; N, 15.48.

EXAMPLE 9

5-[(4-((4-Acetyl-3-hydroxy-2-propylphenyl)methoxy)phenyl)methyl]-2-(5-bromopentanyl)-2H-tetrazole In a procedure similar to Example 5, the following reagents and amounts were combined.
1-[2-Hydroxy-3-propyl-4-((4-(1H-tetrazol-5-ylmethyl)phenoxy)methyl)phenyl]ethanone sodium salt (10 g, 0.026 mol);
1,5-dibromopentane (6.9 g, 0.03 mol);
Potassium carbonate (5 g); and
MEK (150 ml).

The above reaction mixture was stirred at room temperature for 48 hours. Work-up and chromatography were as with Example 5 to yield 4.2 g, 31.3% yield of the 2H-tetrazole-2-isomer of the title product as a light yellow oil: n.m.r. (300 MHz, CDCl₃) δ: 1.0 (t, 3H); 1.5 (m, 2H); 1.6 (m, 2H); 1.9 (m, 2H); 2.0 (m, 2H); 2.6 (s, 3H); 2.7 (t, 2H); 3.4 (t, 2H); 4.2 (s, 2H); 4.55 (t, 2H); 5.1 (s, 2H); 6.9 (d, 2H); 7.0 (d, 1H); 7.3 (d, 2H); 7.6 (d, 1H); 12.7 (s, 1H).

Analysis Calculated for C₂₅H₃₁N₄O₃Br: Theory: C, 58.25; H, 6.06; N, 10.87; Found: C, 58.13; H, 6.13; N, 10.64.

EXAMPLE 10

5-[(4-((4-Acetyl-3-hydroxy-2-propylphenyl)methoxy)phenyl)methyl]-2H-tetrazole-2-(6-hexanenitrile)

5-[(4-((4-Acetyl-3-hydroxy-2-propylphenyl)methoxy)phenyl)methyl]-2-(5-bromopentanyl)-2H-tetrazole (3.9 g, 0.0075 mol) was dissolved in DMSO (30 ml). Potassium cyanide (0.975 g, 0.015 mol) was added and the reaction was slurried at room temperature for 6 hours. Water (250 ml) was added to the slurry and the mixture was extracted with ethyl acetate. The combined ethyl acetate layers were washed with water and brine, dried over sodium sulfate, filtered, and concentrated in vacuo. The residue was chromatographed by HPLC on a silica gel column eluted with a mixture 9:1 toluene:ethyl acetate to yield 2.7 g, 77.1% yield of the title (2H-tetrazole-2-isomer) product: n.m.r. (300 MHz, CDCl$_3$) δ: 1.0 (t, 3H); 1.5 (m, 2H); 1.6 (m, 2H); 1.7 (m, 2H); 2.05 (q, 2H); 2.3 (t, 2H); 2.6 (s, 3H); 2.7 (t, 2H); 4.2 (s, 2H); 4.6 (t, 2H); 5.1 (s, 2H); 6.9 (d, 2H); 7.0 (d, 1H); 7.3 (d, 2H); 7.6 (d, 1 H); 12.7 (s, 1H).

Analysis Calculated for C$_{28}$H$_{37}$N$_5$O$_3$:
Theory: C, 67.66; H, 6.77; N, 15.15;
Found: C, 67.80; H, 6.80; N, 14.99.

EXAMPLE 11

5-[(4-((4-Acetyl-3-hydroxy-2-propylphenyl)methoxy)-phenyl)methyl]-2H-tetrazole-2-(7-heptanenitrile)

In a procedure similar to Example 7, the following reagents and amounts were used:
1-[2-Hydroxy-3-propyl-4-((4-(1H-tetrazol-5ylmethyl)-phenoxy)methyl)phenyl]ethanone sodium salt (10 g, 0.026 mol);
MEK (100 ml);
potassium carbonate: (5 g); and
7bromoheptanonitrile (5.7 g, 0.03 mol).

The reaction mixture was stirred at room temperature for 48 hours. The reaction mixture was worked up in the usual way. The residue was chromatographed by HPLC on a silica gel column, eluted with a mixture of 8:2 toluene: ethyl acetate to yield 2.7 g of the 2H-tetrazole-2-isomer as a light yellow oil: n.m.r. (300 MHz, CDCl$_3$) δ: 1.0 (t, 3H); 1.4 (m, 2H); 1.5 (m, 2H); 1.8 (m, 4H); 2.0 (q, 2H); 2.3 (t, 2H); 2.6 (s, 3H); 2.7 (t, 2H); 4.2 (s, 2H); 4.6 (t, 2H); 5.1 (s, 2H); 6.9 (d, 2H); 7.0 (d, 1H); 7.3 (d, 2H); 7.6 (d, 1H); 12.7 (s, 1H).

Analysis Calculated for C$_{27}$H$_{33}$N$_5$O$_3$: Theory: C, 68.19; H, 6.99; N, 14.73; Found: C, 68.34; H, 7.20; N, 14.49.

EXAMPLE 12

5-[(4-((4-Acetyl-3-hydroxy-2 ethyphenyl)-methoxy)pheny)methyl]-2-(6-bromohexyl)-2H-tetrazole The following reagents and amounts thereof were combined in acetone (50 ml):
1-[2-Hydroxy-3-ethyl-4-((4-(1H-tetrazol-5ylmethyl)-phenoxy)methyl)phenyl]ethanone (8.5 g, 0.0241 mol);
1,6-dibromohexane (7.32 g, 0.03 mol); and
Potassium carbonate (5.3 g, 0.004 mol);

The above mixture was stirred for 24 hours at room temperature. The mixture was poured into water and extracted with ethyl acetate. The ethyl acetate layer was washed with dilute sodium hydroxide solution, dried over magnesium sulfate, and concentrated in in vacuo. The residue was chromatographed by HPLC on a silica gel column eluted first with toluene then a with a mixture of 5% ethyl acetate in toluene. From the chromatography was collected the fractions containing 4 g of the 2H-tetrazole-2-isomer of the title product as an oil: n.m.r.(300 MHz, CDCl$_3$) δ: 1.18 (t, 3H); 1.32 (m, 2H, 1.48 (m, 2H); 1.83 (m, 2H); 2.0 (m, 2H); 2.62 (s, 3H); 2.72 (q, 2H); 3.38 (t, 2H); 4.2 (s, 2H); 4.56 (t, 2H); 5.06 (s, 2H); 6.91 (d, 2H); 7.0 (d, 1H); 7.24 (d, 2H); 7.6 (d, 1H); 12.66 (s, 1H).

Analysis Calculated for C$_{25}$H$_{31}$N$_4$O$_3$Br: Theory: C, 58.75; H, 6.00; N, 10.82; Found: C, 58.42; H, 6.19; N, 10.72.

EXAMPLE 12A

5-[(4-((4-Acetyl-3-hydroxy-2-propylphenyl)-methoxy)phenyl)methyl-2-(6-bromohexyl)-2H-tetrazole In a procedure similar to that of Example 12 above, the following reagents and amounts were combined:
1-[2-Hydroxy-3-propyl-4-((4-(1H-tetrazol-5ylmethyl)-phenoxy)methyl)phenyl]ethanone sodium salt (7.82 g, 0.02 mol);
1,6-dibromohexane (4.88 g, 0.02 mol);
Acetonitrile (100 ml); and
HMPA (50 ml).

The above mixture was stirred at room temperature for 48 hours then the crude product was isolated and chromatographed as in Example 12. This procedure yielded 3.7 g of the 2H-tetrazole-2-isomer: n.m.r. (300 MHz, CDCl$_3$) δ: 1.0 (t, 3H); 1.34 (m, 2H); 1.48 (m, 2H); 1.6 (m, 2H); 1.83 (m, 2H); 2.0 (m, 2H); 2.6 (s, 3H); 2.66 (m, 2H); 3.36 (t, 2H); 4.2 (s, 2H); 4.56 (t, 2H); 5.08 (s, 2H); 6.9 (d, 2H); 7.0 (d, 1H); 7.21 (d, 2H); 7.6 (d, 1H); 12.66 (s, 1H).

Analysis Calculated for C$_{26}$H$_{33}$N$_4$O$_3$Br:
Theory: C, 58.98; H, 6.28; N, 10.58;
Found: C, 59.95; H, 6.47; N, 10.41.

EXAMPLE 13

5-[(4-((4-Acetyl-3-hydroxy-2-ethylphenyl)methoxy)-phenyl)methyl]-2H-tetrazol-2-(6-heptanonitrile)

5-[(4-((4-Acetyl-3-hydroxy-2-ethylphenyl)methoxy)-phenyl)methyl]-2-(6-bromohexyl)-2H-tetrazole (3.7 g, 0.0072 mol) and sodium cyanide (7.2 g) were dissolved in DMSO (25 ml). The mixture was stirred at room temperature for 1 hour then diluted with water and extracted with ethyl acetate. The combined ethyl acetate extracts were washed three times with water then dried over sodium sulfate. The dried extracts were taken to dryness in vacuo to leave 3.2 g of a residue of the title (2H-tetrazole) product: n.m.r. (300 MHz, CDCl$_3$) δ: 1.18 (t, 3H); 1.36 (m, 2H); 1.5 (m, 2H); 1.65 (m, 2H); 2.02 (m, 2H); 2.32 (t, 2H); 2.63 (s, 3H); 2.72 (q, 2H); 4.2 (s, 2H); 4.56 (t, 2H); 5.06 (s, 2H); 6.90 (d, 2H); 7.0 (d, 1H); 7.26 (d, 2H); 7.6 (d, 1H); 12.65 (s, 1H).

Analysis Calculated for C$_{26}$H$_{31}$N$_5$O$_3$: Theory: C, 66.79g; H, 6.95; N, 15.58; Found: C, 65.54; H, 6.23; N, 14.26.

EXAMPLE 14

5-[(4-((4-Acetyl-3-hydroxy-2-propylphenyl)methoxy)-phenyl)methyl]-2H-tetrazole-2-(5-(2,2-dimethylpen-tanenitrile)) and the corresponding 1H-tetrazole-1-isomer In a procedure similar to that of Example 11, the following reagents and amounts were combined:
1-[2-Hydroxy-3-propyl-4-((4-(1H-tetrazol-5ylmethyl)-phenoxy)methyl)phenyl]ethanone sodium salt (9.3 g, 0.024 mol);
MEK (100 ml);
potassium carbonate: (4 g, 0.024 mol);
(4-cyano-3,3-dimethyl)butyl iodide (5.7 g, 0.024 mol).

The above reaction mixture was stirred at room temperature for 24 hours. After the usual work-up, the residue was chromatographed on HPLC on a silica gel column eluted with a mixture of 9:1 toluene:ethyl acetate. The chromatography yielded the 2H-tetrzole-2-isomer of the above title product as an oil: n.m.r. (300 MHz, CDCl$_3$) δ: 1.0 (t, 3H); 1.15 (s, 6H); 1.6 (m, 2H); 2.1 (t, 2H); 2.3 (s, 2H); 2.6 (s, 3H); 2.7 (t, 2H); 4.2 (s, 2H); 4.6 (t, 2H); 5.1 (s, 2H); 6.9 (d, 2H); 7.0 (d, 1H); 7.3 (d, 2H); 7.6 (d, 1H); 12.7 (s, 1H).

Analysis Calculated for C$_{27}$H$_{33}$N$_5$O$_3$: Theory: C, 68.19; H, 6.99; N, 14.73; Found: C, 68.40; H, 7.27; N, 14.51.

The chromatography also yielded the 1H-tetrzole isomer of the above title product as an oil: n.m.r. (300 MHz, CDCl$_3$) δ: 1.0 (t, 3H); 1.1 (s, 6H); 1.6 (m, 2H); 1.7 (t, 2H); 2.15 (s, 2H); 2.6 (s, 3H); 2.7 (t, 2H); 4.15 (t, 2H); 4.25 (s, 2H); 5.1 (s, 2H); 6.9 (d, 2H); 7.0 (d, 1H); 7.2 (d, 2H); 7.6 (d, 1H); 12.7 (s, 1H).

Analysis Calculated for C$_{27}$H$_{33}$N$_5$O$_3$: Theory: C, 68.19; H, 6.99; N, 14.73; Found: C, 70.28; H, 7.29; N, 13.42.

EXAMPLE 15

5-[(4-((4-Acetyl-3-hydroxy-2-propylphenyl)methoxy)-phenyl)methyl]-2-(3-(dimethylamino)propyl)-2H-tetrazole In a procedure similar to that of Example 17 the following reagents and amounts were combined:
5-[(4-((4-Acetyl-3-hydroxy-2-propylphenyl)methoxy)-phenyl)methyl]-2-(3-bromopropyl)-2H-tetrazole (3 g, 0.006 mol);
Acetonitrile (50 ml); and
Dimethylamine (large excess)

The mixture was cooled and stirred at 0° C. for 5 hours. The crude product was isolated and chromatographed as in Example 14, with the exception that the eluant was a 9.5:0.5 methylene chloride:methanol mixture containing an additional 0.5% of diethylamine. The procedure yielded 2.4 g, 88.9% yield of the title (2H-tetrazole-2-isomer) product as a yellow oil: n.m.r. (300 MHz, CDCl$_3$) δ: 1.0 (t, 3H); 1.6 (m, 2H); 2.1 (m 2H); 2.2 (s, 6H); 2.3 (q, 2H); 2.6 (s, 3H); 2.65 (t, 2H); 4.2 (s, 2H); 4.6 (t, 2H); 5.1 (s, 2H); 6.9 (d, 2H); 7.0 (d, 1H); 7.3 (d, 2H); 7.6 (d, 1H); 12.7 (s, 1H).

Analysis Calculated for C$_{25}$H$_{33}$N$_5$O$_3$: Theory: C, 66.50; H, 7.37; N, 15.51; Found: C, 66.71; H, 7.28; N, 15.58.

EXAMPLE 16

5-[(4-((4-Acetyl-3-hydroxy-2-propylphenyl)methoxy)-phenyl)methyl]-1-(3-(dimethylamino)propyl)-1H-tetrazole 5-[(4-((4-Acetyl-3-hydroxy-2-propylphenyl)methoxy)phenyl)methyl]-1-(3-bromopropyl)-1H-tetrazole (2.0 g, 0.004 mol) was added to acetonitrile (40 ml). Dimethylamine (large excess) was cooled in the unopened reagent bottle then added to the acetonitrile solution. The mixture was cooled and stirred at 0° C. for 5 hours then concentrated in vacuo. Water was added to the concentrate and the aqueous solution was extracted with ethyl acetate. The ethyl acetate layers were combined, washed with water, dried over sodium sulfate, filtered, and concentrated to dryness in vacuo. The residue was chromatographed by HPLC (preparatory-scale, silica gel column, eluted isocratically with a mixture of 9.5:0.5 methylene chloride:methanol plus 0.5% diethylamine added) to yield 1.4 g, 77.8% yield of the title product as a yellow oil; n.m.r. (300 MHz, CDCl$_3$) δ: 1.0 (t, 3H); 1.6 (m, 2H); 1.9 (m, 2H); 2.1 (s, 6H; m, 2H); 2.6 (s, 3H); 2.65 (t, 2H); 4.2 (t, 2H); 4.3 (s, 2H); 5.1 (s, 2H); 6.9 (d, 2H); 7.0 (d, 1H); 7.15 (d, 2H); 7.6 (d, 1H); 12.7 (s, 1H).

Analysis Calculated for C$_{25}$H$_{33}$N$_5$O$_3$: Theory: C, 66.50; H, 7.37; N,15.5; Found: C, 66.74; H, 7.22; N, 15.59.

EXAMPLE 17

5-[(4-((4-Acetyl-3-hydroxy-2-propylphenyl)methoxy)-phenyl)methyl]-2-(3-methylthiopropyl)-2H-tetrazole 5-[(4-((4-Acetyl-3-hydroxy-2-propylphenyl)methoxy)phenyl)methyl]-2-(3-bromopropyl)-2H-tetrazole (3.1 g, 0.006 mol) was dissolved in DMSO (20 ml). A large excess of sodium methyl sulfide was added and the reaction mixture was stirred at room temperature for three hours. Water (100 ml) was added and the reaction mixture was extracted with ethyl acetate. The ethyl acetate layers were combined, washed with water and brine, dried over magnesium sulfate, filtered and concentrated in vacuo. The residue was chromatographed by HPLC (preparatory-scale, silica gel column, eluted with a mixture of 9:1 toluene:ethyl acetate) to yield 2.1 g, 77.8% yield of the title product as a yellow oil which crystallized upon standing: n.m.r. (300 MHz, CDCl$_3$) δ: 1.0 (t, 3H); 1.6 (m, 2H); 2.1 (s, 3H); 2.3 (m, 2H); 2.5 (m, 2H); 2.6 (s, 3H); 2.7 (t, 2H); 4.2 (s, 2H); 4.7 (t, 2H); 5.1 (s, 1H); 6.9 (d, 2H); 7.0 (d, 1H); 7.3 (d, 2H); 7.6 (d, 1H); 12.7 (s, 1H).

Analysis Calculated for C$_{24}$H$_{30}$N$_4$O$_3$S: Theory: C, 63.41; H, 6.65; N, 12.32; Found: C, 63.62; H, 6.70; N, 12.70.

EXAMPLE 18

5-[(4-((4-Acetyl-3-hydroxy-2-propylphenyl)methoxy)-phenyl)methyl]-2H-tetrazole-2-(α-(p-tolunitrile))

In a procedure similar to that of Example 11, the following reagents and amounts were combined:
1-[2-Hydroxy-3-propyl-4-((4-(1H-tetrazol-5ylmethyl)-phenoxy)methyl)phenyl]ethanone (11 g, 0.03 mol);
acetone (100 ml);
potassium carbonate (6.9 g, 0.05 mol); and
α-bromo-P-tolunitrile (6.3 g, 0.032 mole).

The above mixture was stirred for 72 hours at 25° C. and the crude product isolated in the usual manner. The residue was chromatographed by HPLC over silica using a toluene 5% ethyl acetate mixture to yield the 2H-tetrazole-2-isomer (5.0 g): n.m.r. (300 MHz, CDCl$_3$) δ: 1.0 (t, 3H); 1.6 (m, 2H); 2.62 (s, 3H); 2.66 (m, 2H); 4.2 (s, 2H); 5.08 (s, 2H); 5.76 (s, 2H); 6.9 (d, 2H); 7.0 (d, 1H); 7.23 (d, 4H); 7.43 (d, 2H); 7.6 (d, 1H); 7.68 (d, 2H); 12.66 (s, 1H).

Analysis Calculated for C$_{28}$H$_{27}$N$_5$O$_3$: Theory: C, 69.84; H, 5.65; N, 14.54; Found: C, 70.85; H, 5.94; N, 13.43.

EXAMPLE 19

5-[(4-((4-Acetyl-3-hydroxy-2-propylphenyl)methoxy)-phenyl)]-2-(3-bromopropyl)-2H-tetrazole 1-[2-Hydroxy-3-propyl-4-((4-(1H-tetrazol-5-yl)phenoxy)methyl)phenyl]ethanone sodium salt (5 g, 0.013 mol), 1,3-dibromopropane (3.5 g, 0.18 mol), and MEK (50 ml) were combined potassium carbonate (4.15 g, 0.025 mol) potassium was added and the reaction mixture was stirred at room temperature overnight. The reaction solution was concentrated under reduced pressure. The volume of the concentrate was doubled by the addition of water and the resultant solution was extracted with ethyl acetate (3×). The ethylacetate layers were combined, washed with water, dried over sodium sulfate, filtered, and concentrated in vacuo. The residue was chromatographed by HPLC (preparatory-scale, silica gel column, eluted with a mixture of 9:1 toluene-:ethyl acetate) to yield 5.0 g, 82% yield of the title product: n.m.r. (300 MHz CDCl$_3$) δ: 1.0 (t, 3H); 1.6 (m, 2H); 2.6 (s and t, 5H); 2.7 (t, 2H); 3.5 (t, 2H); 4.8 (t, 2H); 5.15 (s, 2H); 7.1 (d, 2H); d, 1H); 7.6 (d, 1H); 8.1 (d, 2H); 12.7 (s, 1H).

Analysis Calculated for $C_{22}H_{25}N_4O_3Br$: Theory: C, 55.82; H, 5.32; N, 11.84; Found: C, 55.95; H, 5.28; N, 11.76.

EXAMPLE 20

5-[4-((4-Acetyl-3-hydroxy-2-propylphenyl)methoxy)-phenyl]-2H-tetrazole-2-(4-butyronitrile)

5-[4-((4-Acetyl-3-hydroxy-2-propylphenyl)methoxy)phenyl]-1H-tetrazole (10 g, 0.026 mol) was added to acetone. Potassium carbonate (excess) was added to the solution and the mixture was stirred at room temperature for 30 minutes. 4-Bromobutyronitrile (4.44 g, 3 ml, 0.03 mol) was added and the mixture was stirred overnight at room temperature. Water was added and the resultant mixture was extracted with ethyl acetate. The ethyl acetate layers were treated and chromatographed as in Example 19 to yield 4.8 g, 43.6% yield of the title product: m.p.: 108°–110° C.; n.m.r. (300 MHz, CDCl$_3$) δ: 1.0 (t, 3H): 1.6 (m, 2H): 2.4–2.6 (two sets of multiplets, 4H); 2.6 (s, 3H); 2.7 (t, 2H); 4.8 (t, 2H); 5.2 (s, 2H); 7.0–7.1 (two d, 3H); 7.6 (d, 1H); 8.1 (2, 2H); 12.7 (s, 1H).

Analysis Calculated for $C_{23}H_{25}N_5O_3$: Theory: C, 65.86; H, 6.01; N, 16.07 Found: C, 66.16; H, 6.27; N, 16.50.

EXAMPLE 21

1-[2-Hydroxy-3-propyl-4-[[4-[[1-(1H-tetrazol5ylmethyl-1H-tetrazol-5-yl]methyl]phenoxy]methyl]phenyl]ethanone 5-[(4-((4-Acetyl-3-hydroxy-2-propylphenyl)methoxy)phenyl)methyl]-1H-tetrazole-1-(acetonitrile) (8.6 g, 0.021 mol) was dissolved in DME (100 ml). Tri(n-butyl)tin azide (21.1 g, 0.063 mol) was added and the reaction mixture was stirred and heated at reflux temperature for 3 days. The reaction mixture was cooled and poured into a 50/50 toluene/dilute hydrochloric acid solution (1 liter). The acidified mixture was stirred for several hours, yielding an oil. The solvent was decanted from the oil. The oil was dissolved in ethanol then the ethanol was removed in vacuo. (The ethanol procedure was repeated once). The residue was dissolved in ethyl acetate (200 ml) and hexane was added to the solution until it became cloudy. Upon standing, a precipitate formed from the cloudy solution, the precipitate was collected by filtration to yield 7.7 g of the title product: m.p.: 148°–150° C.; n.m.r. (300 MHz, DMSO-d$_6$) δ: 0.9 (t, 3H); 1.5 (q, 2H); 2.6–2.8 (m overlapping peaks 5H); 4.3 (s, 2H); 5.1 (s, 2H); 6.1 (s, 2H); 6.9 (d, 2H); 7.1 (d, 1H); 7.2 (d, 2H); 7.8 (d; 1H); 12.7 (s, 1H).

Analysis Calculated for $C_{22}H_{24}N_8O_3$: Theory: C, 58.92; H, 5.37; N, 24.99; Found: C, 59.20; H, 5.44; N, 24.72.

EXAMPLE 22

1-[2-hydroxy-3-(propyl)-4-[[4-[[2-(1H-tetra-zol-5-ylmethyl)-2H-tetrazol-5-yl]methyl]phenoxyl]methyl]phenyl]ethanone 5-[(4-((4-Acetyl-3-hydroxy-2-propylphenyl)methoxy)phenyl)methyl]-2H-tetrazole-2-(acetonitrile) (6.9 g, 0.017 mol) was dissolved in DME (100 ml). Tri(n-butyl)tin azide (17 g, 0.05 mol) was added and the reaction mixture was stirred and heated to reflux temperature for 3 days. The reaction mixture was cooled and poured into a 50/50 mixture of dilute aqueous hydrochloric acid and toluene. The resultant oil was collected and precipitated from a mixture of ethyl acetate/hexane to yield 2.3 g of the title product: m.p. 137°–139° C.; n.m.r.: (300 MHz, DMSO-d$_6$) δ: 0.9 (t, 3H); 1.5 (m, 2H); 2.6–2.7 (s and t overlapping, 5H); 4.2 (s, 2H), 5.2 (s, 2H); 6.4 (s, 2H); 6.9 (d, 2H); 7.1 (d, 1H); 7.2 (d, 2H); 7.8 (d, 1H); 12.7 (s, 1H).

Analysis Calculated for $C_{22}H_{24}N_8O_3$: Theory: C, 58.92; H, 5.39; N, 24.99; Found: C, 59.15; H, 5.41; N, 24.74.

EXAMPLE 23

1-[2-Hydroxy-3-propyl-4-[[4-[[1-[3-(1H-tetrazol5-yl)propyl]-1H-tetrazol-5-ylmethyl]phenoxy]phenyl]ethanone 5-[(4-((4-Acetyl-3-hydroxy-2-propylphenyl)-methoxy)phenyl)methyl]-1H-tetrazole-1-(4-butyronitrile) (6.2 g, 0.014 mol) was dissovled in DME (100 ml). Tri(n-butyl)tin azide (14.5 g, 0.043 mol) was added and the reaction mixture was stirred at reflux temperature for 3 days then cooled to room temperature. The reaction mixture was poured into a 50/50 mixture of toluene/dilute aqueous hydrochloric acid and the resultant mixture was stirred for 1 hour. The oil thus obtained was isolated by decanting the solvents. The oil was twice dissolved in ethanol and taken to dryness. The residue was dissolved in ethyl acetate (150 ml). Hexane was added to the ethyl acetate solution until the the solution became cloudy. Upon standing an oil resulted. The oil was chromatographed by HPLC (preparatory-scale, silica gel column, eluted with a gradient of neat methylene chloride to a mixture of 9:1 methylene chloride:methanol). The resultant product-containing fractions were combined and taken to dryness. The residue was dissolved in ethyl acetate. Hexane was added to the solution to the point of cloudiness. An oil formed upon standing and the solution was cooled in the refrigerator overnight. A solid formed when the cooled solution was stirred. The solid was collected by filtration. The solid was title product: m.p. 121°–123° C.; n.m.r. (300 MHz, DMSO-d$_6$) δ: 6: 0.9 (t, 3H); 1.5 (q, 2H); 2.5 (q, 2H); 2.6 (s and t, 5H); 2.9 (t, 2H); 4.3 (s, 1H); 4.5 (t, 2H); 5.1 (s, 2H); 6.9 (d, 2H); 7.0 (d, 1H); 7.2 (d, 2H); 7.8 (d, 1H); 12.7 (s, 1H).

Analysis Calculated for $C_{24}H_{28}N_8O_3$: Theory: C, 60.49; H, 5.92; N, 23.51; Found: C, 60.47; H, 5.81; N, 23.51.

EXAMPLE 24

1-2[-Hydroxy-3-propyl-4[[4-[[2-[3-(1H-tetra- zol-5-yl)propyl]-2H-tetrazol-5-yl]methyl]phenoxy]methyl]-phenyl]ethanone 5-[(4-((4-Acetyl-3-hydroxy-2-propylphenyl)methoxy)phenyl)methyl]-2H-tetrazole-2-(4-butyronitrile) (7 g, 0.016 mol) was dissolved in DME (50 ml). Tri(nbutyl)- tin azide (16.3 g, 0.048 mol) was added and the reaction mixture was stirred and heated to reflux temperature for 3 days. The reaction mixture was cooled to room temperature and poured into a mixture of toluene/hexane/10% aqueous hydrochloric acid (125 ml/125 ml/ (25 ml in 225 ml)). The resultant precipitate was collected by filtration and recrystallized from a mixture of ethanol and water to yield 5.6 g, 71.8% yield of the title product: m.p 118°–121° C.; n.m.r. (300 MHz, DMSO-$d_6$) δ0.9 (t, 3H); 1.5 (m, 2H); 2.4 (m, 2H); 2.6–2.7 (s, 3H; t, 2H); 2.9 (t, 2H); 4.1 (s, 2H); 4.7 (t, 2H); 5.1 (s, 2H); 6.9 (d, 2H); 7.1 (d, 1H); 7.2 (d, 2H); 7.8 (d, 1H); 12.7 (s, 1H).

Analysis Calculated for $C_{24}H_{28}N_8O_3$: Theory: C, 60.49; H, 5.92; N, 23.52; Found: C, 60.88; H, 5.85; N, 23.51.

The sodium salt was formed by dissolving the above free tetrazole (12.55 g, 0.0263 mol) in ethanol. 1N sodium hydroxide solution (26.3 ml) was added and the solution was stirred for 30 minutes). The solvent was removed in vacuo. A foam formed which was dried under vacuum at 30°–40° C. and was 11.8 g, 85.3% yield of the sodium salt of the title compound: m.p. 85°–90° C.; n.m.r. (300 MHz, DMSO-$d_6$) δ: 0.9 (t, 3H); 1.4–1.6 (q, 2H); 2.2 (q, 2H); 2.6–2.8 (overlapping peaks 7H); 4.2 (s, 2H), 4.7 (t, 2H); 5.1 (s, 2H); 6.9 (d, 2H); 7.0 (d, 1H) 7.2 (d, 2H); 7.8 (d, 1H); 12.7 (s, 1H).

Analysis Calculated for $C_{24}H_{27}N_8O_3Na$: Theory: C, 57.82; H, 5.4; N, 22.48; Found: C, 57.24; H, 5.79; N, 21.46.

EXAMPLE 25

1-[2-Hydroxy-3-propyl-4-[[4-[[1-[4-1H-tetrazol-5-yl)butyl]-1H-tetrazol-5-yl]methyl]phenoxy]methyl]-phenyl]ethanone and the corresponding sodium salt 5-[(4-((4-Acetyl-3-hydroxy-2-propylphenyl)methoxy)phenyl)methyl]-1H-tetrazole-1-(5-valeronitrile) (6.7 g, 0.015 mol) was dissolved in DME (100 ml). Tri(n-butyl)tin azide (15.2 g, 0.045 mol) was added then the reaction mixture was heated to reflux temperature and stirred for 3 days. The mixture was cooled and poured into a 1:1 mixture of toluene:10% aqueous hydrochloric acid solution. The resultant mixture was stirred for several days until a precipitate formed. The precipitate was collected by filtration and recrystallized from a mixture of ethyl acetate:hexane to yield 3.6 g, 49% of the title product: m.p.: 96°–98° C.; n.m.r. (300 MHz, DMSO-$d_6$) δ: 0.9 (t, 2H); 1.5 (q, 2H); 1.6–1.8 (overlapping peak, 6H); 2.6–2.7 (overlapping peaks, 5H); 2.75 (t, 2H); 4.3 (s, 2H); 4.4 (t, 2H); 5.1 (s, 2H); 7.0 (d, 2H); 7.05 (d, 1H); 7.2 (d, 2H); 7.8 (d, 1H); 12.7 (s, 1H).

Analysis Calculated for $C_{25}H_{30}N_8O_3$: Theory: C, 61.21; H, 6.16; N, 22.84; Found: C, 60.98; H, 6.05; N, 22.71.

EXAMPLE 26

1-[2-Hydroxy-3-propyl-4-[[4-[[2-[4-(1H-tetrazol-5-yl)butyl]tetrazol-5-yl]methyl]phenoxy]methyl]phenyl]ethanone 5-(4-((4-Acetyl-3-hydroxy-2-propylphenyl)-methoxy)-phenyl)methyl]2H-tetrazole-2-(5-valeronitrile) (9.5 g, 0.02 mol) was dissolved in DME (100 ml). Tri(n-butyl)tin azide (21.6 g, 0.06 mol) was added and the reaction mixture was heated to reflux temperature and stirred for 3 days. The reaction mixture was cooled and poured into a 1:1 mixture of toluene: 10% aqueous hydrochloric acid. After stirring for 2 hours, the organic phase was separated, dried over sodium sulfate and taken to dryness in vacuo. The resultant residue was chromatographed by HPLC (preparatory-scale, silica gel column, eluted with a gradient of neat methylene chloride to a mixture of 9:1 methylene chloride:methanol). The product-containing fractions were combined and concentrated then dissolved in ethyl acetate. Hexane was added to the ethyl acetate solution until the solution became cloudy. An oil formed from the cloudy solution. The mixture was stored overnight in the refrigerator resulting in a precipitate (6.3 g, 64.3%) of the title product: m.p.: 119°–123° C.; n.m.r. (300 MHz, DMSO-$d_6$): δ: 0.9 (t, 3H); 1.55 (q, 2H); 1.7 (q, 2H); 1.95 (q, 2H); 2.8 (overlapping peaks, 5H); 2.9 (t, 2H); 4.15 (s, 2H); 4.7 (t, 2H); 5.1 (s, 2H); 6.9 (d, 2H); 7.1 (d, 1H); 7.2 (d, 2H); 7.8 (d, 1H); 12.7 (s, 1H).

Analysis Calculated for $C_{25}H_{30}N_8O_3$: Theory: C, 61.21; H, 6.16; N, 22.84; Found: C, 61.03; H, 6.31; N, 22.62.

EXAMPLE 27

1-[2-Hydroxy-3-propyl-4-[[4-[[2-[6-(1H-tetrazol-5-yl)hexyl]-2H-tetrazol-5-yl]methyl]phenoxy]methyl]-phenyl]ethanone 5-[(4-((4-Acetyl-3-hydroxy-2-propylphenyl)methoxy)phenyl)methyl]-2H-tetrazole-2-(7-heptanenitrile) (2.4 g, 0.005 mol) was dissolved in glyme. Tri(n-butyl) tin azide (5.12 g, 0.015 mol) was added and the reaction mixture was heated to reflux temperature and stirred for 3 days. The reaction mixture was cooled to room temperature and poured into a 1:1 mixture of toluene-hexane:10% aqueous hydrochloric acid. The acidic mixture was stirred for 2 hours resulting in a precipitate. The precipitate was filtered and recrystallized from a mixture of ethanol and water to yield 1.0 g of the title product: m.p.: 110°–113° C.; n.m.r. (300 MHz, DMSO-$d_6$) δ: 0.9 (t, 3H); 1.2–1.4 (m, 2H; m, 2H); 1.5 (m, 2H); 1.7 (m, 2H); 1.9 (m, 2H); 2.6–2.7 (s, 3H, t, 2H); 2.8 (t, 2H); 4.1 (s, 2H); 4.6 (t, 2H); 5.1 (s, 1H); 6.9 overlapping (d, 2H); 7.1 (d, 2H); 7.2 (d, 2H); 7.8 (d, 1H); 12.7 (s, 1H);

Analysis Calculated for $C_{27}H_{34}N_8O_3$: Theory: C, 62.53; H, 6.61; N, 21.61; Found: C, 62.73; H, 6.83; N, 21.63.

EXAMPLE 28

1-[4-[[4-[[2-3,3-Dimethyl-4-(1H-tetrazol5-yl)butyl]-2H-tetrazol-5-yl]methyl]phenoxy]methyl]-2-hydroxy-3-propylphenyl]ethanone 5-[(4-((4-Acetyl-3-hydroxy-2-propylphenyl)methoxy)phenyl)methyl]-2H-tetrazole-2-(5-(2,2-dimethylpentanenitrile)) (4.2 g, 0.008 mol) was dissolved in diglyme (35 ml). Tri(n-butyl)tin azide (8.6 g, 0.025 mol) was added and the reaction mixture was heated to reflux temperature and stirred for 3 days. The mixture was cooled to room temperature and poured into a 1:1 mixture of toluene/hexane:10% aqueous hydrochloric acid (250 ml). An oil resulted from the acidic mixture. The oil was isolated by decanting the solvent. The oil was dissoved in ethanol then the ethanol solution was evaporated to dryness. The residue was chromatographed by HPLC (preparatory-scale, silica gel column, eluted with a gradient of neat methylene chloride to a mixture of 9:1 methylene chloride:methanol) to yield 1.5 g, 38.9% yield of the title product as an oil: n.m.r. (300 MHz, DMSO-$d_6$) $\delta$: 1.0 (t, 3H); 1.1 (s, 6H); 1.6 (q, 2H); 2.0 (t, 2H); 2.6 (s, 3H); 2.7 (t, 2H); 2.9 (s, 2H); 4.2 (s, 2H); 4.7 (t, 2H); 5.1 (s, 2H); 6.9 (d, 2H); 7.0 (d, 1H); 7.2 (d, 2H); 7.6 (d, 1H); 12.7 (s, 1H).

Analysis Calculated for $C_{27}H_{34}N_8O_3$: Theory: C, 62.53; H, 6.61; N, 21.61; Found: C, 62.38; H, 6.40; N, 21.40.

EXAMPLE 29

1-[2-Hydroxy-3-propyl-4-[[4-[[2-[5-(1H-tetrazol-5-yl)pentyl]-2H-tetrazol-5-yl]methyl]phenoxy]methyl]phenyl]ethanone sodium salt 5-[(4-((4-Acetyl-3-hydroxy-2-propylphenyl)methoxy)phenyl)methyl]-2H-tetrazole-2-(6-hexanenitrile) (2.5 g, 0.005 mol) was dissolved in DME. Tri(n-butyl)tin azide (5.5 g, 0.016 mol) was added and the mixture was stirred and heated at reflux temperature for 3 days. The reaction mixture was cooled to room temperature and poured into a mixture of 1:1 toluene/hexane:10% aqueous hydrochloric acid solution (200 ml). The acidic mixture yielded an oil. The solvent was poured from the mixture and the oil thus isolated was dissolved in ethanol. The ethanol solution was taken to dryness and the resultant residue was chromatographed by HPLC (preparatory-scale, silica gel column, eluted with a gradient of neat methylene chloride to a mixture of 9:1 methylene chloride/methanol). The chromatography yielded a 1.3 g, 51.6% yield of an oil of the free acid title product.

The sodium salt of the above title product was formed by first dissolving the above oil composed of the free acid in ethanol. 1N Sodium hydroxide solution (2.6 ml) was added, then the solvent was removed in vacuo. A foam formed which was dried under vacuum at 30°–40° C. to yield 1.4 g of the sodium salt of the title product: m.p. 70°–80° C.; n.m.r. (300 MHz, DMSO-$d_6$) $\delta$: 0.9 (t, 3H); 1.3 (m, 2H); 1.5-1.7 (m, 4H); 1.9 (m, 2H); 2.6 (t, 2H); 2.7 (s, 3H); t, 4.1 (s, 2H); 4.6 (t, 2H); 5.1 (s, 2H); 6.9 (d, 2H); 7.0 (d, 1H); 7.2 (d, 2H); 7.8 (d, 2H); 12.7 (s, 1H).

Analysis Calculated for $C_{26}H_{32}N_8O_3Na$: Theory: C, 59.30; H, 5.93; N, 21.28; Found: C, 59.76; H, 5.93; N, 20.68.

EXAMPLE 30

5-[[4-[(4-Acetyl-3-hydroxy-2-propylphenyl)methoxy]phenyl]methyl]-1H-tetrazole-1-acetic acid Ethyl 5-[(4-((4-Acetyl-3-hydroxy-2-(n-propyl)phenyl)methoxy)phenyl)methyl]-1H-tetrazole-1-(2-acetate) (7.7 g, 0.017 mol) and 5N aqueous sodium hydroxide solution (10 ml) were combined, stirred, and heated to reflux temperature. Methanol (50 ml) was added to the solution after the mixture began to reflux. After 1 hour at reflux temperature, the solution was poured into water and the resultant solution was made acidic by the addition of aqueous hydrochloric acid. The acidified solution was allowed to stand overnight then made basic with 5N sodium hydroxide solution. The aqueous layer was separated and made acidic again by the addition of 5N aqueous hydrochloric acid. The acidified aqueous layer was extracted with a mixture of 2:1 ether-:isopropyl alcohol. The organic phase was separated and then taken to dryness. The resultant residue was dissolved in the minimum amount of hot DMF. Water was added to the DMF solution to induce crystallization and the mixture was allowed to stand overnight. The precipitate was collected by filtration and washed with ethanol. The collected precipitate was then dried in a vacuum oven at 40° C. This procedure yielded 2.8 g of the title product: m.p. 205°–210° C. n.m.r. (270 MHz, DMSO-$d_6$) $\delta$: 0.95 (t, 3H); 1.5 (m, 2H); 2.63 (m, 5H); 4.24 (s, 2H); 5.12 (s, 2H); 5.38 (s, 2H); 6.94 (d, 2), 7.04 (d, 1H); 7.2 (d, 2H); 7.8 (d, 1H); 12.7 (s, 1H).

Analysis Calculated for $C_{22}H_{24}N_4O_5$: Theory: C, 62.25; H, 5.70; N, 13.20; Found: C, 62.22; H, 5.94; N, 12.98.

EXAMPLE 31

5-[[4-[(4-Acetyl-3-hydroxy-2-propylphenyl)methoxy]phenyl]methyl]-2H-tetrazole-2-acetic acid Ethyl 5-(4-((4-Acetyl-3-hydroxy-2-propylphenyl)methoxy)phenyl)methyl]-2H-tetrazole-2-(2-acetate) (7.5 g, 0.017 mol) absolute ethanol (100 ml), and aqueous sodium hydroxide solution (5N, 10 ml) were combined, stirred and heated to reflux temperature. After 1 hour the reaction solution was poured into water and the resultant solution was made acidic by the addition of 5N hydrochloric acid. After standing overnight, the acidic solution was extracted with ethyl acetate and the organic layer was dried over a mixture of sodium sulfate and magnesium sulfate. The organic layer was then evaporated in vacuo to an oil that yielded some crystals on standing. The mixture was chromatographed by HPLC (preparatory-scale, silica gel column, eluted with 2:8 methanol:methylene chloride solvent system) to yield two products in fractions 3–6. These fractions were combined, and the solvent was removed. The residue was heated in 20 ml of EtOH and 2.5 mL 5N NaOH for 3 hours. After cooling, the reaction mixture was diluted with 1N hydrochloric acid (to a total volume of 50 ml). The resultant precipitate was collected by filtration. The precipitate was recrystallized from 90% EtOH ($H_2O$) to yield 0.6 g of title product: m.p. 87°–90° C.: n.m.r. (300 MHz, $CDCl_3$) $\delta$: 1.0 (t, 3H); 1.6 (m, 2H); 2.62 (s, 3H); 2.64 (m, 2H), 4.22 (s, 2H); 5.06 (s, 2H), 5.42 (s, 2H); 6.9 (d, 2H), 7.0 (d, 1H); 7.24 (d, 2H); 7.6 (d, 1H); 12.64 (s, 1H).

Analysis Calculated for $C_{22}H_{24}N_5O_4$: Theory: C, 62.25; H, 5.70; N, 13.20; Found: C, 62.12; H, 5.83; N, 12.95.

EXAMPLE 32

5-[[4-[[4-Acetyl-3-hydroxy-2-propylphenyl)methoxy]phenyl]methyl]-1H-tetrazole-1-butyric acid Ethyl 5-[(4-((4-Acetyl-3-hydroxy-2-propylphenyl)methoxy)phenyl)methyl]-1H-tetrazole-1-(4-butyrate) (4.8 g, 0.010 mol) was dissolved in 2B absolute ethanol and aqueous sodium hydroxide solution (5N, 6 ml) was added. The solution was stirred and heated to reflux temperature for 2 hours then cooled to room temperature. The cooled reaction solution was poured into water and the resultant solution was made acidic with the addition of concentrated hydrochloric acid. The acidified solution was extracted with ethyl acetate (2×), and the ethyl acetate layers were dried over sodium sulfate/silicone dioxide, filtered and taken to dryness in vacuo. The resultant residue was chromatographed by HPLC (preparatory-scale, silica gel column, 5% methanol in methylene chloride) to yield 2.4 g of the title product: m p.: 106°–108° C. n.m.r. (300 MHz, CDCl$_3$) δ: 0.96 (t, 3H); 1.58 (m, 2H); 2.05 (m, 2H); 2.34 (t, 2H); 2.60 (s, 3H); 2.64 (m, 2H); 4.22 (m, 4H); 5.05 (s, 2H); 6.9 (d, 2H); 6.98 (d, 1H); 7.12 (d, 2H); 7.6 (d, 1H); 12.66 (s, 1).

Analysis Calculated for $C_{24}H_{28}N_4O_5$: Theory: C, 63.70; H, 6.24; N, 12.38; Found: C, 63.48; H, 6.13; N, 12.16.

EXAMPLE 33
5-[(4-[(4-Acetyl-3-hydroxy-2-propylphenyl) methoxy]phenyl)methyl]-2H-tetrazole-2-butanoic acid Ethyl 5-[(4-((4-Acetyl-3-hydroxy-2-propylphenyl)-methoxy)phenyl)methyl]-2H-tetrazole-2-(4-butyrate) (11.2 g, 0.0233 mol) was dissolved in 2B absolute ethanol. To the solution was added aqueous sodium hydroxide solution (14 ml, 5N) and the solution was heated to reflux and stirred for 2 hours. The reaction mixture was cooled and poured into water and the resultant solution was made acidic with concentrated hydrochloric acid. The acidic solution was allowed to stand overnight and the resultant solid was collected by vacuum filtration. The solid was dried in vacuo at 40° C. The dried solid was recrystallized from ethanol, filtered, and dried in vacuo to yield 7.8 g of the title product: m.p.: 92°–94° C.; n.m.r. (300 MHz, DMSO-d$_6$) δ: 0.92 (t, 3H); 1.52 (m, 2H); 2.1 (m, 2H); 2.26 (t, 2H); 2.62 (m, 5H); 4.16 (s, 2H); 4.66 (t, 2H); 5.15 (s, 2H); 6.95 (d, 2H); 7.05 (d, 1H); 7.2 (d, 2H); 7.8 (d, 1H); 12.7 (s, H).

Analysis Calculated for $C_{24}H_{28}N_4O_5$: Theory: C, 63.70; H, 6.24; N, 12.38; Found: C, 63.75; H, 6.34; N, 12.70.

EXAMPLE 34
5-[(4-[(4-Acetyl-3-hydroxy-2-propylphenyl)methoxy]-phenyl)methyl]-1H-tetrazol-1-valeric acid Ethyl 5-[(4-((4-Acetyl-3-hydroxy-2-propylphenyl)-methoxy)phenyl)methyl]-1H-tetrazole-1-(5-valerate) (4.0 g, 0.0081 mol) was dissolved in 2B ethanol. Sodium hydroxide solution (5N, 5 ml) was added and the solution was stirred at reflux temperature for 2 hours. The solution was cooled to room temperature, poured into water, and the resultant solution was made acidic with concentrated hydrochloric acid. The acidified solution was extracted with ethyl acetate (3×). The ethyl acetate layers were combined and dried over of sodium sulfate/silicon dioxide, filtered and evaporated to dryness in vacuo. The residue was chromatographed by HPLC (preparatory-scale, silica gel column, 5% methanol in methylene chloride) to give 2.7 g of the title product: n.m.r. (300 MHz, CDCl$_3$) δ: 0.98 (t, 3H); 1.56 (m, 4H); 1.76 (m, 2H); 2.3 (t, 2H); 2.62 (s, 3H); 2.64 (m, 2H); 4.13 (t, 2H); 4.24 (s, 2H); 5.08 (s, 2H); 6.9 (d, 2H); 6.98 (d, 1H); 7.12 (d, 2H); 7.6 (d, 1H); 12.66 (s, 1H).

Analysis Calculated for $C_{25}H_{30}N_4O_5$: Theory: C, 64.36; H, 6.48; N, 12.01; Found: C, 63.05; H, 6.72; N, 11.03.

EXAMPLE 35
5-[(4-[(4-Acetyl-3-hydroxy-2-propylphenyl)methoxy]-phenyl)methyl]-2H-tetrazole-2-valeric acid Ethyl 5-[(4-((4-Acetyl-3-hydroxy-2-propylphenyl)-methoxy)phenyl)methyl]-2H-tetrazole-2-(5-valerate) (11.8 g, 0.0239 mol) was dissolved in 2B absolute ethanol. Aqueous sodium hydroxide solution (5N, 14.3 ml) was added to the solution and the solution was stirred at reflux temperature for 2 hours. The crude product was isolated from the reaction mixture as in Example 34 and chromatographed by HPLC (preparatoryscale, silica gel column, eluted with a mixture 19:1 methylene chloride:methanol eluant) to yield approximately 7.0 g of the title product: n.m.r. (300 MHz, CDCl$_3$) δ: 1.0 (t, 3H); 1.64 (m, 4H); 2.06 (m, 2H); 2.4 (t, 2H); 2.62 (s, 3H); 2.64 (m, 2H); 4.2 (s, 2H); 4.6 (t, 2H); 5.08 (s, 2H); 6.9 (d, 2H); 7.0 (d, 1H); 7.24 (d, 2H); 7.6 (d, 1H); 12.66 (s, 1H).

Analysis Calculated for $C_{25}H_{30}N_4O_5$: Theory: C, 64.36; H, 6.48; N, 12.01; Found: C, 64.59; H, 6.68; N, 11.80.

EXAMPLE 36
1-2-Hydroxy-3-propyl-4-[[4-[2-[3-(1H-tetrazol-5-yl)propyl]-2H-tetrazol-5-yl]phenoxy]methyl]-phenyl]ethanone ethanone 5-[4-((4-Acetyl-3-hydroxy-2-propylphenyl)-methoxy)-phenyl]-2H-tetrazole-2-(4-butyronitrile) (4.5 g, 0.11 mol) and tri(n-butyl)tin azide (33.2 g, 0.10 mol) were combined in DME. The resultant reaction solution was heated and stirred at reflux temperature for 3 days then poured into a 50/50 mixture of toluene/10% aqueous hydrochloric acid. The resultant precipitate was collected by filtration and recrystallized from a mixture of ethanol and water to yield 4 g, 80% of the title product: m.p. 194°–196° C.

n.m.r.: (300 MHz, DMSO-d$_6$) δ: 0.9 (t, 3H); 1.6 (m, 2H); 2.4–2.6 (m, 4H); 2.7 (t +s, 5H); 3.0 (t, 2H); 4.95 (t, 2H); 5.25 (s, 2H); 7.1 (d, 1H); 7.2 (d, 2H); 7.8 (d, 1H); 8.0 (d, 2H); 12.7 (s, 1H).

Analysis Calculated for $C_{22}H_{29}N_8O_3$: Theory: C, 59.73; H, 5.67; N, 24.23; Found: C, 60.01; H, 5.87; N, 24.03.

EXAMPLE 37
1-[4-[[4-[2-[3-(Dimethylamino)propyl]-2H-tetrazol-5-yl]phenoxy]methyl]-2-hydroxy-3-propyl-phenyl]ethanone 5-[4-((4-Acetyl-3-hydroxy-2-propylphenyl)methoxy)phenyl]-2-(3-bromopropyl)-2H-tetrazole (2.8 g, 0.006 mol) was dissolved in acetonitrile and cooled to 10 approximately 0° C. Dimethylamine (anhydrous, excess) was cooled in the reagent bottle before it was opened then added to the cool acetonitrile solution. The solution was maintained at approximately 0° C. with an ice bath while it was stirred (approximately 5 hours). The reaction mixture was then concentrated in vacuo. Water was added and the resultant solution was extracted with ethyl acetate. The ethyl acetate layers were combined, washed with water and dried over sodium sulfate. The dried ethyl acetate layers were concentrated and the resultant residue was chromatographed by HPLC (preparatoryscale, silica gel column, eluted isocratically with a mixture of 9.5 : 0.5 methylene chloride:methanol to which 0.05% of diethylamine had been added to yield 2.3 g, 88.5% yield of the title product: m.p. 89°–91° C.; n.m.r.: (300 MHz, CDCl$_3$) δ: 1.0 (t, 2H); 1.6 (m, 2H); 2.1 (t, 2H); 2.2 (s, 6H); 2.3, (t, 2H); 2.4 (t, 2H); 2.6 (s, 3H); 2.7 (t, 2H); 4.7 (t, 2H); 5.2 (s, 2H); 7.1 (2d, 3H); 7.6 (d, 1H); 8.1 (d, 2H); 12.7 (s, 1H).

Analysis Calculated for C$_{24}$H$_{31}$N$_5$O$_3$: Theory: C, 65.88; H, 7.14; N, 16.01; Found: C, 66.11; H, 7.08; N, 16.23.

EXAMPLE 38

1-[2-Hydroxy-3-propyl-4-[[4-[[2-[[4-(1H-tetrazol-5-yl)phenyl]methyl]-2H-tetrazol-5-yl]methyl]-phenoxy]methyl]phenyl]ethanone A mixture of 4.81 g (0.01 mol) of 5-[(4-((4- acetyl-3-hydroxy-2-propylphenyl)methoxy)phenyl)methyl]2H-tetrazol-2-(α-(p-tolunitrile)) and 12.18 g (0.037 mol) of tri(n-butyl)tin azide in 100 mL of 1,2-dimethoxyethane was heated to maintain reflux for 48 hrs, cooled, poured into 1 liter of 5% HCl, 200 mL toluene, and 300 mL of hexane, stirred 1 hr, and the precipitate filtered. Two recrystallizations from 90% EtOH gave 2.3 g of the title compound: m.p. 86°–88° C.; n.m.r. (300 MHz, DMSO-d$_6$) δ: 0.9 (t, 3H); 1.52 (m, 2H); 2.62 (m, 5H); 4.2 (s, 2H); 5.12 (s, 2H); 6.0 (s, 2H); 6.93 (d, 2H); 7.06 (d, 1H); 7.2 (d, 2H); 7.56 (d, 2H); 7.8 (d, 1H); 8.06 (d, 2H); 12.7 (s, 1H);

Analysis Calculated for C$_{28}$H$_{28}$N$_8$O$_3$: Theory: C, 64.11; H, 5.38; N, 21.36; Found: C, 62.79; H, 4.98; N, 20.50.

EXAMPLE 39

5-[(4-((4-Acetyl-3-hydroxy-2-propylphenyl)methoxy)-phenyl)methyl]-2-(3-methylsulfinylpropyl)-2H-tetrazole 5-(4-((4-Acetyl-3-hydroxy-2-propylphenyl) methoxy)phenyl)methyl]-2-(3-methylthiopropyl)-2H-tetrazole (2.3 g, 0.005 mol) was dissolved in methanol (75 ml). Sodium periodate (1.1 g, 0.00525 moles) was dissolved in water (25 ml) and the aqueous solution was added to the methanol solution. The reaction mixture was stirred overnight at room temperature then diluted with water (100 ml). The diluted reaction mixture was extracted with ethyl acetate. The organic extracts were combined, washed with water and brine, dried over magnesium sulfate, filtered and concentrated. The concentrate was chromatographed by preparatory-scale HPLC (silica column) eluted isocratically with a mixture of 8:2 toluene:ethyl acetate to yield an oil of the title product: n.m.r. (300 MHz, CDCl$_3$) δ: 1.0 (t, 3H); 1.6 (m, 2H); 2.5 (t, 2H); 2.55 (s, 3H); 2.6 (s, 3H); 2.6–2.8 (m, 4H); 4.2 (s, 2H); 5.7–5.8 (m, 2H); 5.1 (s, 2H); 6.8 (d, 2H); 7.0 (d, 2H); 7.2–7.3 (d, 2H); 7.6 (d, 2H); 12.7 (s, 1H).

Analysis Calculated for C$_{24}$H$_{30}$N$_4$O$_4$S: Theory: C, 61.26; H, 6.63; N, 9.97; Found: C, 61.05; H, 6.68; N, 10.08.

EXAMPLE 40

5-[(4-((4-Acetyl-3-hydroxy-2-propylphenyl)methoxy)-phenyl)methyl]-2-(3-methylsulfonylpropyl)-2H-tetrazole 5-[(4-((4-Acetyl-3-hydroxy-2-propylphenyl)methoxy)phenyl)methyl]-2-(3-methylthiopropyl)-2H-tetrazole (2.0 g, 0.0044 mol) was dissolved in methylene chloride. Meta-chloroperbenzoic acid (1.6 g) was added slowly to the methylene chloride solution. The reaction mixture was stirred for one hour at room temperature then diluted with methylene chloride. The mixture was washed with saturated aqueous sodium bicarbonate solution and water. The layers were separated and the organic layer was dried over magnesium sulfate, filtered and concentrated in vacuo. The concentrate was precipitated from ethanol/water to yield the title product: m.p. 89°–91° C.; n.m.r. (300 MHz, DMSO-d$_6$) δ: 0.9 (t, 3H); 1.4–1.6 (m, 2H); 2.3–2.4 (m, 2H); 2.5 (t, 1H); 2.6–2.7 (overlapping peaks, 5H); 3.2 (t, 2H); 3.3 (s, 3H); 4.2 (s, 2H); 4.8 (t, 2H); 5.15 (s, 2H); 6.9 (d, 2H); 7.1 (d, 1H); 7.2 (d, 2H); 7.8 (d, 1H); 12.7 (s, 1H).

Analysis calculated for C$_{24}$H$_{30}$N$_4$O$_5$S: Theory: C, 59.24; H, 6.21; N, 11.51; Found: C, 59.38; H, 6.34; N, 11.47.

EXAMPLE 41

Hard gelatin capsules are prepared using the following ingredients:

| | Quantity (mg/capsule) |
|---|---|
| 1-[2-Hydroxy-3-propyl-4[[4-[[2-[3-(lH—tetrazol-5-yl)propyl]-2H—tetrazol-5-yl]methyl]phenoxy]-methyl]phenyl]ethanone | 250 |
| Starch | 200 |
| Magnesium stearate | 10 |

The above ingredients are mixed and filled into hard gelatin capsules in 460 mg quantities.

EXAMPLE 42

A tablet is prepared using the ingredients below:

| | Quantity (mg/tablet) |
|---|---|
| 1-[2-Hydroxy-3-propyl-4[[4-[[2-[3-(lH—tetrazol-5-yl)propyl]-2H—tetrazol-5-yl]methyl]phenoxy]-methyl]phenyl]ethanone | 250 |
| Cellulose, microcrystalline | 400 |
| Silicon dioxide, fumed | 10 |
| Magnesium stearate | 5 |

The components are blended and compressed to form tablets each weighing 665 mg.

EXAMPLE 43

An aerosol solution is prepared containing the following components:

| | Weight % |
|---|---|
| 1-[2-Hydroxy-3-propyl-4[[4-[[2-[3-(lH—tetrazol-5-yl)propyl]-2H—tetrazol-5-yl]methyl]phenoxy]-methyl]phenyl]ethanone | 0.25 |
| Ethanol | 30.00 |
| Propellant 11 (trichlorofluoromethane) | 10.25 |
| Propellant 12 (Dichlorodifluoromethane) | 29.75 |
| Propellant 114 (Dichlorotetrafluoroethane) | 29.75 |

The active compound is dissolved in the ethanol and the solution is added to the propellant 11, cooled to −30° C. and transferred to a filling device. The required amount is then fed to a container and further filled with the pre-mixed propellants 12 and 114 by means of the cold-filled method or pressure-filled method. The valve units are then fitted to the container.

EXAMPLE 44

Tablets each containing 60 mg of active ingredient are made up as follows:

| | |
|---|---|
| 1-[2-Hydroxy-3-propyl-4-[[4-[[2-[4-(1H—tetrazol-5-yl)butyl]tetrazol-5-yl]-methyl]phenoxy]methyl]phenyl]ethanone | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 45

Capsules each containing 80 mg of medicament are made as follows:

| | |
|---|---|
| 1-[2-Hydroxy-3-propyl-4[[4-[[2-[3-(1H—tetrazol-5-yl)propyl]-2H—tetrazol-5-yl]methyl]phenoxy]methyl]phenyl]ethanone | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quanitities.

EXAMPLE 46

Suppositories each containing 225 mg of active ingredient are made as follows:

| | |
|---|---|
| 1-[4-[[4-[[2-[3,3-Dimethyl-4-(1H—tetrazol-5-yl)butyl]-2H—tetrazol-5-yl]methyl]phenoxy]methyl]-2-hydroxy-3-propylphenyl]ethanone | 225 mg |
| Unsaturated or saturated fatty acid glycerides to | 2,000 mg |

The active ingredient is passed through a No. 60 mesh U.S. sieve and suspended in the fatty acid glycerides previously melted using the minimum heat necessary. The mixture is then poured into a suppository mold of nominal 2 g capacity and allowed to cool.

EXAMPLE 47

Suspensions each containing 50 mg of medicament per 5 ml dose are made as follows:

| | |
|---|---|
| 1-[2-Hydroxy-3-propyl-4[[4-[[2-[3-(1H—tetrazol-5-yl)propyl]-2H—tetrazol-5-yl]methyl]phenoxy]methyl]phenyl]ethanone | 50 mg |
| Sodium carboxymethyl cellulose | 50 mg |
| Sugar | 1 g |
| Methyl paraben | 0.05 mg |
| Propyl paraben | 0.03 mg |
| Flavor | q.v. |
| Color | q.v. |
| Purified water to | 5 ml |

The medicament is passed through a No. 45 mesh U.S. sieve and mixed with the sodium carboxymethylcellulose, sugar, and a portion of the water to form a suspension. The parabens, flavor and color are dissolved and diluted with some of the water and added, with stirring. Sufficient water is then added to produce the required volume.

We claim:

1. A compound of the formula $$R_1\text{-CO-}\underset{OH}{\underset{|}{\text{Ar}}}(R_3)(R_2)\text{-}(C)_w(R_4)(R_5)\text{-}Z\text{-Ar}(R_c)(R_d)\text{-}(CH_2)_n\text{-[Tet]}$$

wherein:
$R_1$ is $C_1$ to $C_3$ alkyl;
$R_2$ is $C_1$ to $C_6$ alkyl or $C_3$ to $C_6$ alkenyl;
$R_3$ is a hydrogen atom, chloro, bromo, nitro, or a group of the formula $$-NR_aR_b$$

wherein $R_a$ and $R_b$ are the same or different and are a hydrogen atom, $C_1$ to $C_4$ alkyl, phenyl, benzyl, or $C_1$ to $C_4$ acyl;
$R_4$ and $R_5$ are the same or different and are a hydrogen atom or $C_1$ to $C_3$ alkyl;
W is from one to six;
Z is O, S or a group of the formula $$-NR_e,$$

(wherein $R_e$ is a hydrogen atom, $C_1$ to $C_4$ alkyl, $C_1$ to $C_4$ acyl, phenyl, or benzyl);
n is 0 to 6;
$R_c$ and $R_d$ are the same or different and are hydrogen, hydroxy, halo or an ether group of the formula $-O-(C_1-C_6$ alkyl);
[Tet] is a disubstituted 1H- or 2H-tetrazolyl ring of the formula $$\begin{array}{c} N \\ \diagup \diagdown \\ -\!\!\!-\!\!\!\parallel \quad N \\ N-\!\!\!-\!\!\!-\!\!\!-N-L-A; \end{array}$$

$$\begin{array}{c} N \\ \diagup \diagdown \\ -\!\!\!-\!\!\!\parallel \quad N \\ A-L-N-\!\!\!-\!\!\!-\!\!\!-N; \end{array}$$

-continued

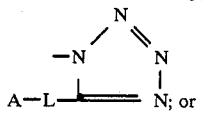

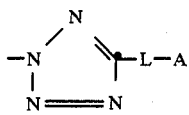

wherein:
L is
(1) $C_1$ to $C_{10}$ alkylidene; or
(2) a group of the formula

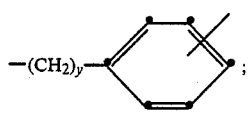

p' wherein y is 1 to 3 (and the phenyl ring is bonded to A);
A is
(1) 5-(tetrazolyl);
(2) carboxy;
(3) —$NR_fR_g$, wherein $R_f$ and $R_g$ are the same or different and are a hydrogen atom, $C_1$ to $C_4$ alkyl, phenyl, benzyl or $C_1$ to $C_4$ acyl; or
(4) a group of the formula

wherein q is 0, 1 or 2 and $R_h$ is $C_1$ to $C_4$ alkyl, phenyl or benzyl;
or a pharmaceutically-acceptable base addition salt thereof.

2. A compound of claim 1, wherein:
$R_1$ is methyl;
$R_2$ is n-propyl;
$R_3$, $R_4$, $R_5$, $R_c$, $R_d$ are a hydrogen atom;
Z is 0;
W is 1;
n is 0 or 1;
[Tet] is a group of the formula:

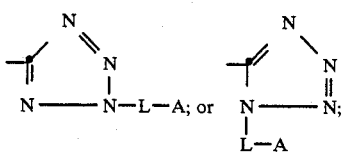

L=
1) $C_1$ to $C_6$ alkylidene; or
(2) a group of the formula

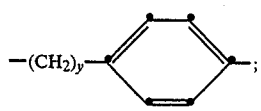

wherein y is one (and the phenyl ring is also bonded to (A);
A is (1) 5-(tetrazolyl);
(2) a group of the formula —$NR_fR_g$ 'wherein $R_f$ and $R_g$ are each methyl;
(3) a group of the formula

wherein $R_h$ is methyl; or
(4) a carboxylic acid;
or a pharmaceutically-acceptable base addition salt thereof.

3. A compound of claim 2, wherein A is 5-(tetrazolyl) and n is one.

4. A compound of claim 3, wherein [Tet]group is of the formula:

5. A compound of claim 4, wherein L is methylene, dimethylene, trimethylene, tetramethylene, pentamethylene, hexamethylene 2,2-dimethyltetramethylene (wherein the C-1 position is bonded to -A); or a group of the formula

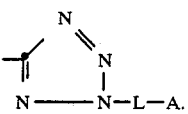

(wherein the phenyl group is also bonded to —A).

6. A compound of claim 5, wherein L is trimethylene.

7. A compound of claim 6, which comprises the sodium salt thereof.

8. A compound of claim 2, wherein A is a group of the formula —COOH and n is one.

9. A compound of claim 8, wherein L is methylene, trimethylene or tetramethylene.

10. A compound of claim 9, wherein [Tet] is a group of the formula

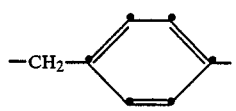

11. A compound of claim 10, wherein L is tetramethylene.

12. A compound of claim 3, wherein [Tet] is a group of the formula:

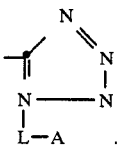

13. A compound of claim 12, wherein L is methylene, trimethylene or tetramethylene.

14. A compound of claim 13, which comprises the sodium salt thereof.

15. A compound of the formula

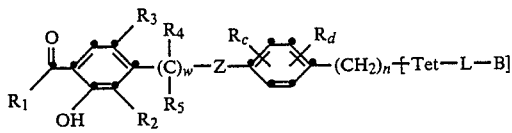

wherein:
$R_1$ is $C_1$ to $C_3$ alkyl;
$R_2$ is $C_1$ to $C_6$ alkyl or $C_3$ to $C_6$ alkenyl:
$R_3$ is a hydrogen atom, chloro, bromo, nitro, or a group of the formula

wherein $R_a$ and $R_b$ are the same or different and are a hydrogen atom, $C_1$ to $C_4$ alkyl, phenyl, benzyl, or $C_1$ to $C_4$ acyl;
$R_4$ and $R_5$ are the same or different and are a hydrogen atom or $C_1$ to $C_3$ alkyl;
W is from one to six;
Z is O, S or a group of the formula

(wherein $R_e$ is a hydrogen atom, $C_1$ to $C_4$ alkyl, phenyl, benzyl or $C_1$ to $C_4$ acyl);
n is 0 to 6;
$R_c$ and $R_d$ are the same or different and are a hydrogen atom; hydroxy, halo or an ether group of the formula —O—($C_1$–$C_6$ alkyl);
[Tet-L-B] is a disubstituted 1H- or 2H-tetrazolyl ring of the formula

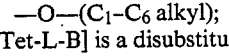

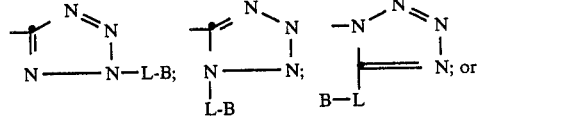

wherein:
L is
(1) $C_1$ to $C_{10}$ alkylidene; or
(2) a group of the formula

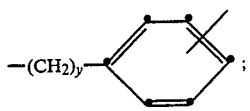

wherein y is 1 to 3 (and the phenyl ring is also bonded to (B); and
B is
(1) cyano;
(2) halo; or
(3) a group of the formula —COOR$_6$, wherein R$_6$ is ethyl or a carboxy-protecting group.

16. A compound of claim 15, wherein:
$R_1$ is methyl;
$R_2$ is n-propyl;
$R_3$, $R_4$, $R_5$, $R_c$, $R_d$ are each hydrogen;
Z is O;
W is 1;
n is 0 or 1;
[Tet-L-B] is a disubstituted 1H- or 2H-tetrazolyl ring of the formula:

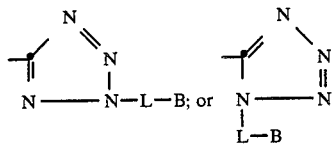

L is
(1) $C_1$ to $C_6$ alkylidene; or
(2) a group of the formula

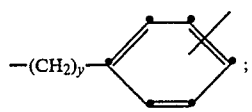

wherein y is one (and the phenyl ring is also bonded to B); and
B is cyano, bromo, or ethyl ester.

17. A compound of claim 16, wherein B is cyano and n is one.

18. A compound of claim 17, wherein [Tet-L-B] is a group of the formula

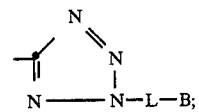

and L is
(1) methylene, trimethylene, tetramethylene, pentamethylene, hexamethylene or 2,2-dimethylbutylene (wherein the C-1 position is bonded to B); or
(2) a group of the formula

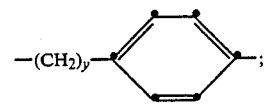

(wherein the phenyl group is bonded to B).

19. A compound of claim 18, wherein L is trimethylene.

20. A compound of claim 17, wherein [Tet-L-B] is of the formula

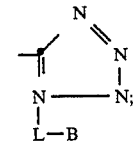

and L is methylene, trimethylene or tetramethylene.

21. A compound of claim 16, wherein n is one and B an ethyl ester.

22. A compound of claim 21, wherein L is methylene, trimethylene or tetramethylene.

23. A compound of claim 22, wherein [Tet-L-B] is a group of the formula:

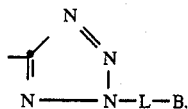

24. A compound of claim 16, wherein B is bromo and n is one.

25. A compound of claim 24, wherein L is trimethylene, pentamethylene or hexamethylene.

26. A compound of claim 25, wherein [Tet-L-B] is a group of the formula

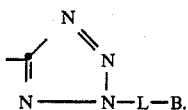

27. A compound of claim 25, wherein L is trimethylene and [Tet-L-B] is a group of the formula:

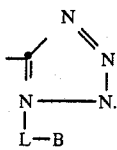

28. A pharmaceutical formulation, which comprises a therapeutically-effective amount of a compound of claim 1 and a pharmaceutically-acceptable carrier.

29. A pharmaceutical formulation, which comprises a therapeutically-effective amount of a compound of claim 2 and a pharmaceutically-acceptable carrier.

30. A pharmaceutical formulation, which comprises a therapeutically-effective amount of a compound of claim 6 and a pharmaceutically-acceptable carrier.

31. A pharmaceutical formulation, which comprises a therapeutically-effective amount of the compound of claim 7 and a pharmaceutically-acceptable carrier.

32. A method of treating a mammal suffering from or susceptible to any condition characterized by an excessive release of leukotrienes $C_4$, $D_4$, and $E_4$, which comprises administering to said mammal a leukotriene antagonizing amount of a compound of claim 1.

33. A method of treating a mammal suffering from or susceptible to any condition characterized by an excessive release of leukotrienes $C_4$, $D_4$, and $E_4$, which comprises administering to said mammal a leukotriene antagonizing amount of a compound of claim 2.

34. A method of treating a mammal suffering from or susceptible to any condition characterized by an excessive release of leukotrienes $C_4$, $D_4$, and $E_4$, which comprises administering to said mammal a leukotriene antagonizing amount of a compound of claim 6.

35. A method of treating a mammal suffering from or susceptible to any condition characterized by an excessive release of leukotrienes $C_4$, $D_4$, and $E_4$, which comprises administering to said mammal a leukotriene antagonizing amount of a compound of claim 7.

36. A method of treating a mammal suffering from or susceptible to an immediate hypersensitivity reaction of the type represented by asthma, which comprises administering to said mammal a therapeutically-effective amount of a compound of claim 1.

37. A method of treating a mammal suffering from or susceptible to an immediate hypersensitivity reaction of the type represented by asthma, which comprises administering to said mammal a therapeutically-effective amount of a compound of claim 2.

* * * * *